US006204361B1

(12) United States Patent
Carpino et al.

(10) Patent No.: US 6,204,361 B1
(45) Date of Patent: Mar. 20, 2001

(54) METHOD OF PEPTIDE SYNTHESIS

(75) Inventors: Louis A. Carpino; Dumitru Ionescu, both of Amherst, MA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 09/200,344

(22) Filed: Nov. 25, 1998

Related U.S. Application Data

(62) Division of application No. 08/588,187, filed on Jan. 18, 1996, now Pat. No. 5,849,954.

(51) Int. Cl.$^7$ .............................. C07K 5/00; C07C 261/00
(52) U.S. Cl. .................. 530/334; 530/333; 530/338; 530/339; 530/340; 530/341; 560/161; 544/235; 544/253; 544/262; 544/334
(58) Field of Search ................................. 530/333, 334, 530/338, 339, 340, 341; 560/161; 544/235, 253, 262, 334

(56) References Cited

U.S. PATENT DOCUMENTS

| 4,069,048 | 1/1978 | Tsubota et al. . | |
|---|---|---|---|
| 5,644,029 | * 7/1997 | Carpino ................................. | 530/333 |
| 5,750,767 | * 5/1998 | Carpino et al. ....................... | 560/161 |

OTHER PUBLICATIONS

Carpino, L., "1–Hydroxy–7–azabenzotriazole. An Efficient Peptide Coupling Additive, "J. Am. Chem. Soc. 1993, 115, pp. 4397–4398.

Carpino, et al., "Advantageous Applications of Azabenzotriazole (Triazolopyridine)–based Coupling Reagents to Solid–phase Peptide Synthesis," J. Chem. Soc., Chem. Commun. 1994, pp. 201–203.

Carpino, et al., "Racemization Studies During Solid–Phase Peptide Synthesis Using Azabenzotriazole–Based Coupling Reagents," Tetrahedron Letters 1994, 35, pp. 2279–2282.

Colton, et al., "Aluminum–27 N.M.R. Studies of Aluminum Fluoro Complexes in Dichloromethane Solution", Aust. J. Chem., 1989, 42 1605–9.

Ehrlich, et al., "Synthesis of Cyclic Peptides via Efficient New Coupling Reagents," Tetrahedron Letters 1993, 34, pp. 4781,4784.

Kundu, et al., "Racemization studies with 1(B–naphthalenesulfonyloxy)–benzotriazole (NSBT)–An efficient peptide coupling reagent," Indian Journal of Chemistry 1989, 28B, pp. 604–605.

Landini, et al., "Convenient Procedures for the Preparation of Lipophilic Quaternary Onium Fluorides, Hydrogendifluorides and DiHydrogentrifluourides via Ion Exchange in Two–Phase Systems," Synthesis 1988, pp. 953–954.

Abstract 1979:491910 Document No. 91:91910 to Ogilvie, et al., Nucleic Acids Res. 6(6), 2261–73 (1979).

Abstract 1979:137769 Document No. 90:137769 to Ogilvie, et al., Tetra Lett. vol. 35, 3203–6 (1978).

Caplus Abstract No. 1980:620812 to Uson, et al., J. Organomet. Chem. (1980) ,194(3), pp. 271–275.

Merrifield, Science vol. 150 pp. 178–184, Oct. 1965.*

Ueki et al., Chem. Lett. pp. 721–24, 1993*

* cited by examiner

*Primary Examiner*—Bennett Celsa
(74) *Attorney, Agent, or Firm*—Scully, Scott, Murphy & Presser

(57) ABSTRACT

The present invention relates to a process for forming an N-α-amino protected amino acid fluoride in situ by reacting an N-α-amino protected amino acid with an ionic fluoride salt in the presence of a peptide coupling agent. It is also directed to the use of the amino acid fluoride thus formed in peptide synthesis.

98 Claims, No Drawings

METHOD OF PEPTIDE SYNTHESIS

This application is a divisional of Ser. No. 08/588,187 (Jan. 18, 1996) now U.S. Pat. No. 5,849,954.

GOVERNMENT SUPPORT

This work has been supported by grants from the National Institutes of Health GM-09706 and the National Science Foundation (CHE 9314083). The Government has certain rights in the invention.

BACKGROUND OF THE INVENTION

1. Field of the Invention

The present invention relates to a new process for effecting peptide synthesis. More specifically, it relates to a new process for preparing an amino acid fluoride, and also to the use thereof in peptide synthesis. Furthermore, the present invention relates to new reagents for preparing the amino acid fluorides.

2. Background of the Invention

Amino acid fluorides have been shown to be a convenient and highly efficient reagent for both solution and solid phase peptide synthesis. When used in peptide synthesis, the peptide formed therefrom is produced in high yield and relatively pure form, with minimal racemization. Furthermore, it has been shown that there are many other advantages associated with the use of amino acid fluorides in peptide synthesis. For example, the acid fluorides allow the syntheses of peptides which incorporate highly-hindered amino acids, such as α-amino isobutyric acid (Aib) and α-ethylalanine (e.g., isovaline, Iva), and the like. Furthermore, amino acid fluorides exhibit several advantages relative to other amino acid halides, e.g., amino acid chlorides or bromides, in the coupling reaction and formation of peptides. For example, unlike the other amino acid halides, amino acid fluorides can accommodate t-butyl side chain protecting groups. Moreover, conversion to the corresponding oxazolone in the presence of t-organic base does not occur, thus avoiding the danger of racemization. Furthermore, the coupling reactions occur readily in the complete absence of an organic base, again avoiding possible racemization.

Moreover, another advantage of amino acid fluorides is that they are easily synthesized from the corresponding amino acid and are isolable in crystalline form. They are generally stable and have a long shelf life.

In view of these advantages, it is highly desirable to utilize amino acid fluorides in peptide synthesis. Thus, peptide synthesis can be effected by first preparing a N-α-amino protected amino acid fluoride and then utilizing this amino acid fluoride as a coupling agent to produce the desired peptide.

Unfortunately, when employing FMOC amino acid fluorides in practical peptide synthesis, difficulties were encountered in the case of two amino acids, arginine and histidine. In the latter case, while FMOC—His (Trt)—F has been synthesized and used in coupling reactions, its long term shelf stability is in doubt. For sulfonamide-protected arginine derivatives (e.g., FMOC—Arg (Pbf)—OH or FMOC—Arg—(Pmc)—OH)), the corresponding acid fluorides could not be synthesized due to their facile cyclization to the corresponding lactam.

Thus, investigations were conducted to improve the efficiency thereof and to overcome these problems. It was felt that the efficiency of the overall process would be enhanced if the amino acid fluoride were produced in situ. Thus, Carpino et al., as described in *JACS* 95, 117, 5401, developed a new uronium-style reagent TFFH, 1, which

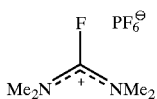

has been shown to act as a coupling reagent which acts via in situ conversion to an acid fluoride:

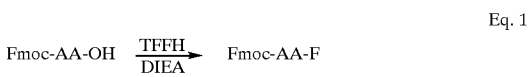

Eq. 1

Although a useful technique, especially since TFFH is relatively inexpensive, a disadvantage of this method is the need to use a basic reagent, such as N,N-diisopropylethylamine (DIEA) in the activation step (Eq. 1). Indeed, the speed of conversion of the acid to the acid fluoride increases with the number of equivalents of DIEA used (1 eq<<2 eqs<3 eqs<4 eqs).

Although this technique was more efficient than methods heretofore used in peptide coupling, scientific investigations were conducted to improve upon this reagent. It was believed that the in situ process for the preparation of protected amino acid fluorides and the overall process of peptide synthesis would be improved if a method could be found to generate amino acid fluorides in situ without the presence of a basic reagent. The present inventors have found such a method. Moreover, the present in situ process overcomes the difficulties discussed hereinabove with histidine and arginine.

SUMMARY OF THE INVENTION

Accordingly, the present invention is directed to a process of preparing a N-α-amino protected amino acid fluoride in situ by reacting a N-α-amino protected amino acid or acylating derivative thereof in the presence of a coupling agent with an ionic fluoride salt. In a preferred embodiment, the anion has the formula:

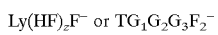  I wherein
z is 0, 1, 2, 3, 4, 5, 6, 7, 8, 9, or 10;
y is 0 or 1;
L is $TG_1G_2G_3G_4$;
T is a Group IV element consisting of Si, Ge, Sn and Pb;
$G_1$, $G_2$, $G_3$ and $G_4$ are independently halogen, hydrogen, alkyl, aryl, aryl alkyl, cycloalkyl or cycloalkyl alkyl.

The present invention is also directed to the preparation of peptides from the in situ preparation of acid fluorides in accordance with the procedure described hereinabove. Finally, the present invention is directed to the novel fluoride salts useful in the in situ preparation of amino acid fluorides.

DETAILED DESCRIPTION OF THE PRESENT INVENTION

As indicated hereinabove, an aspect of the present invention is directed to the in situ synthesis of an N-α-amino protected amino acid fluoride from an N-α-amino protected amino acid or acylating derivative thereof and an ionic fluoride salt in the presence of a coupling agent.

The term "amino acid" is a term of art that is readily understood by the skilled artisan.

As used herein, the term "amino acid" refers to an organic acid containing both a basic amino group ($NH_2$) and an acidic carboxyl group (COOH). Therefore, said molecule is amphoteric and exists in aqueous solution as dipole ions. (See, "The Condensed Chemical Dictionary", 10th ed. edited by Gessner G. Hawley, Van Nostrand Reinhold Company, London, Eng. p.48 (1981)). The preferred amino acids are the α-amino acids. They include, but are not limited to the 25 amino acids that have been established as protein constituents. They must contain at least one carboxyl group and one primary or secondary amino group on the amino acid molecule. They include the naturally occurring amino acids. For example, they include such proteinogenic amino acids as alanine, valine, leucine, isoleucine, norleucine, proline, hydroxyproline, phenylalanine, tryptophan, methionine, glycine, serine, threonine, cysteine, cystine, tyrosine, asparagine, glutamine, aspartic acid, glutamic acid, lysine, hydroxylysine, ornithine, arginine, histidine, naphthylalanine, penicillamine, β-alanine, isovaline, α-amino isobutyric acid, and the like.

A N-α-amino protected amino acid designates an amino acid in which the α-amino group contains a blocking group. These type of blocking groups (also designated as protecting groups) are well known in the art. Examples include 9-fluorenylmethyloxy-carbonyl(FMOC), 2-chloro-1-indanyl methoxy carbonyl (CLIMOC), and benz-[f]-indene-3-methyloxycarbonyl (BIMOC) and dbd-TMOC which are discussed in U.S. Pat. Nos. 3,835,175, 4,508,657, 3,839,396, 4,581,167, 4,394,519, 4,460,501 and 4,108,846, and the contents thereof are incorporated herein by reference as if fully set forth herein. Moreover, other amino protecting groups such as 2-(t-butyl sulfonyl)-2-propenyloxycarbonyl (Bspoc) and benzothiophene sulfone-2-methoxycarbonyl (Bsmoc) are discussed in copending application, U.S. patent application Ser. No. 364,662 and the subject matter therein is incorporated herein by reference. Other amino protecting groups include those described in an article entitled "Solid Phase Peptide Synthesis" by G. Barany and R. B. Merifield in *Peptides,* Vol. 2, edited by E. Gross and J. Meienhoffer, Academic Press, New York, N.Y., pp. 100–118 (1980), the contents of which are incorporated herein by reference. These N-amino protecting groups include such groups as FMOC, Bspoc, Bsmoc, t-butyloxycarbonyl (BOC), t-amyloxycarbonyl (Aoc), β-trimethylethyloxycarbonyl (TEOC), adamantyloxycarbonyl (Adoc), 1-methylcyclobutyloxycarbonyl (Mcb), 2-(p-biphenylyl) propyl-2-oxycarbonyl (Bpoc), 2-(p-phenylazophenyl) propyl-2-oxycarbonyl (Azoc), 2,2-dimethyl-3,5-dimethyloxybenzyloxycarbonyl (Ddz), 2-phenylpropyl-2-oxycarbonyl (Poc), benzyloxycarbonyl (Cbz), p-toluenesulfonyl aminocarbonyl (Tac), o-nitrophenylsulfenyl (Nps), dithiasuccinoyl (Dts), phthaloyl, piperidino oxycarbonyl, formyl, trifluoroacetyl and the like.

The preferred protecting groups can be placed into five categories:

1) a base labile N-α-amino acid protecting group such as FMOC, and the like.
2) protecting groups removed by acid, such as Boc, TEOC, Aoc, Adoc, Mcb, Bpoc, Azoc, Ddz, Poc, Cbz, 2-furanmethyloxycarbonyl (Foc), p-methoxybenzyloxycarbonyl (Moz), Nps, and the like.
3) protecting groups removed by hydrogenation such as Dts, Cbz.
4) protecting groups removed by nucleophiles, such as Bspoc, Bsmoc and Nps and the like.
5) protecting groups derived from carboxylic acids, such as formyl, acetyl, trifluoroacetyl and the like, which are removed by acid, base or nucleophiles.

It will be apparent to one skilled in the art, that in the course of protein synthesis, it may be necessary to protect certain side chains of the amino acids to prevent unwanted side reactions. For example, it may be necessary to protect the hydroxyl group on the side chain of tyrosine, serine, or threonine in order to prevent these groups from interfering with the desired reactions. This is a common problem in peptide synthesis and many procedures are available for protecting the functional groups on the side chains of the amino acids. Such procedures for protecting various functional groups are known to one skilled in the art and are described in the treatise entitled "The PEPTIDES", Vol. 2, Edited by E. Gross and J. Meienhoffer, Academic Press, NY, N.Y., pp. 166–251 (1980), and the book entitled "Protective Groups in Organic Synthesis", by T. W. Green, John Wiley and Sons, New York, 1981, the contents of both being incorporated herein by reference.

The various protecting groups for the N-α-amino group and side chains are described in U.S. Pat. No. 5,360,928 and copending application entitled "Cyclopropyl Based O and N and S-Protecting Groups" having Serial Number U.S. Ser. No. 08/221,226, assigned to the same assignee as that of the present application. The contents of both are incorporated herein by reference as if fully set forth herein.

Thus, the term "N-α-amino protected amino acid" encompasses those amino acids having a protecting group on the α-amino group. The side chain thereof may or may not have a blocking group; it may not be necessary, as with some amino acids which do not have on the side chain a functional group, i.e., a group which is reactive with the reagents or products formed under peptide forming conditions if not protected by a blocking group. The amino acids which do not have a functional group thereon include such amino acids as glycine, alanine, valine and the like. On the other hand, the side chain may have a functional group, but it may or may not be protected. However, if being used in peptide synthesis, it is preferred that the functional group be protected by a side chain blocking group.

An acylating derivative of said amino acid refers to an acylating group that replaces the OH group on the α-carboxyl group. Examples include acid halides, i.e., Br, I or Cl; esters, such as aryl, alkyl, arylalkyl, cycloalkyl or cycloalkyl alkyl esters; alkyl anhydrides and the like.

A peptide coupling agent is another term of art readily understood by the skilled artisan. They include the dehydrating agents normally used in peptide formation. Examples of coupling agents are carbodiimides, such as N,N-dicyclohexylcarbodiimide (DCC), N,N-Diisopropylcarbodiimide (DIC), N-ethyl-N-(3-dimethylaminopropyl) carbodiimide (EDC), and the like, the active esters, such as esters of 1-hydroxybenzotriazole (HOBt), N-ethyloxycarbony-2-ethyloxy-1,2-dihydroquinone (EEDQ), propane phosphonic acid anhydride (T3P) etc. Other coupling agents are described in copending application entitled "New Reagents For Peptide Couplings", having U.S. Ser. No. 08/127,675, which has been assigned to the present assignee, the contents of which are incorporated by reference.

The aforementioned application discloses coupling agents of the formula:

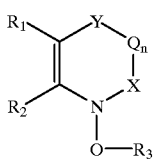

and N-oxides thereof and salts thereof wherein $R_1$ and $R_2$ taken together with the carbon atoms to which they are attached form a heteroaryl ring wherein said heteroaryl ring is an oxygen, sulfur or nitrogen containing heteroaromatic containing from 3 and up to a total of 13 ring carbon atoms, said heteroaryl may be unsubstituted or substituted with lower alkyl or an electron-donating group;

Y is O, $NR_4$, $CR_4R_5$;

$R_4$ and $R_5$ are independently hydrogen or lower alkyl;

X is $CR_6R_7$ or $NR_6$;

$R_6$ and $R_7$ are independently hydrogen or lower alkyl; or $R_6$ and $R_7$ taken together form an oxo group or when n=0, $R_4$ and $R_6$ taken together may form a bond between the nitrogen or carbon atom of Y and the nitrogen or carbon atom of X;

Q is ($CR_8R_9$) or ($NR_8$);

when n is 1, $R_4$ and $R_8$ taken together may form a bond between the ring carbon or nitrogen atom of Q and the ring carbon or nitrogen atom of $R_8$;

each n is independently 0, 1 or 2;

$R_3$ is lower alkyl carbonyl, aryl carbonyl, lower aryl alkyl carbonyl, a positively charged electron withdrawing group, $SO_2R_{14}$ or

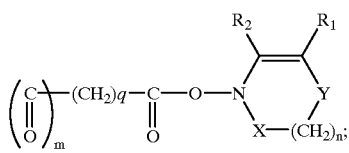

$R_{14}$ is lower alkyl, aryl or lower arylalkyl;

q is 0–3;

$R_8$ and $R_9$ are independently hydrogen or lower alkyl or $R_7$ and $R_8$ taken together with the carbon to which they are attached form an aryl ring, and m is 0 or 1.

Preferred embodiments for $R_3$ include lower alkyl carbonyl, aryl carbonyl, lower aryl alkyl carbonyl and a positively charged electron withdrawing group. It is preferred that $R_3$ is not a phosphonium cation.

The term "electron withdrawing groups" as defined herein refers to a group that will draw electrons to itself more than a hydrogen atom would if it occupied the same position in the molecule. S, J. March, *Advanced Organic Chemistry*, 3rd Ed., John Wiley & Sons P. 17 (1985). They include such groups as nitro, monohaloalkyl, dihaloalkyl, trihaloalkyl (e.g., $CF_3$), halo, formyl, lower alkanoyl, lower alkylsulfonyl, lower alkylsulfonyl, and the like.

A positively charged electron withdrawing group is an electron withdrawing group bearing a positive charge and forming a stable bond to a N-hydroxide (N—O). These types of groups are well known in the art. Examples include uronium groups, e.g.,

imino cations e.g.,

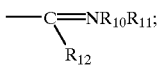

and the like, wherein $R_{10}$, $R_{11}$, $R_{12}$ and $R_{13}$ are independently hydrogen or lower alkyl, lower alkoxy lower alkyl or $R_{10}$ and $R_{12}$ taken together with the atoms to which they are attached form a ring containing up to 6 ring atoms and up to a total of 5 ring carbon atoms or $R_{12}$ and $R_{13}$ or $R_{10}$ and $R_{11}$ taken together with the nitrogen atom to which they are attached may form a 5 or 6 membered heterocyclic ring containing up to a total of 5 ring carbon atoms. The heterocyclic ring thus formed preferably contains one nitrogen atom. It is preferred that $R_{10}$ and $R_{11}$ and $R_{12}$ and $R_{13}$, when both are present, are the same. It is especially preferred that $R_{10}$, $R_{11}$, $R_{12}$, $R_{13}$, whenever are present, are the same.

Preferred cyclic uronium and imino groups have the formula

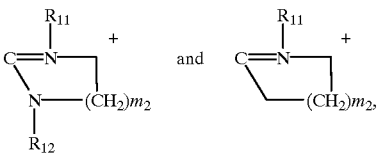

respectively, wherein $R_{11}$ and $R_{12}$ are as defined hereinabove and $M_2$ is 0 or 1.

It is preferred that compounds of Formula II have the formula:

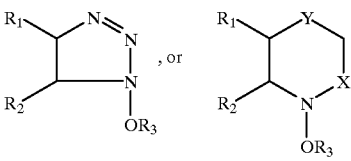

wherein $R_1$, $R_2$, $R_3$, Y and X are as defined hereinabove.

Other preferred compounds of Formula II have the formula:

IIA

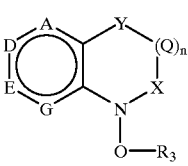

or N-oxides thereof wherein Q, Y, X, $R_3$, n, $R_4$, $R_5$, $R_6$, $R_7$, $R_8$, $R_9$ and $R_{14}$ are as defined hereinabove, A is N or $CR_{15}$;

D is $CR_{16}$ or N;

E is $CR_{17}$ or N;

G is $CR_{19}$ or N; and $R_{15}$, $R_{16}$, $R_{17}$ and $R_{18}$ are independently hydrogen or lower alkyl or an electron donating group or $R_{16}$ and $R_{17}$ taken together form an aryl ring, but at least one of A, D, E, G is N.

It is preferred that no more than two of A, D, E, G are N. It is most preferred that only one of A, D, E, G is N. Further, it is preferred that $R_{15}$, $R_{16}$, $R_{17}$ or $R_{18}$ are hydrogen or an electron-donating group, as defined herein. The preferred electron donating groups are lower dialkylamino, especially N, N-dimethylamino and lower alkoxy, e.g. methoxy.

Preferred compounds of Formula IIA have the formulae:

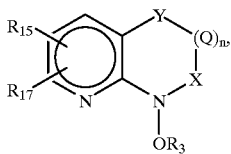

III

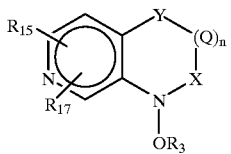

IV

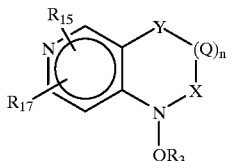

V

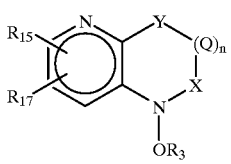

VI or N-oxides thereof
wherein Y, X, n, Q and $R_3$ are as defined hereinabove and $R_{15}$ and $R_{17}$ are independently lower alkyl and more preferably hydrogen or an electron donating group.

Preferred compounds of Formula II also have the formula

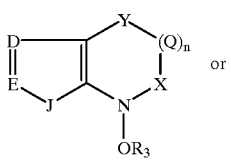

VII or

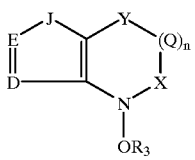

VIII or N-oxides thereof
wherein $R_8$, $R_9$, n, Q, D, E, X and Y are as defined hereinabove and J is $NR_{15}$, O, $CR_{15}R_{19}$ or $S(O)p$, and p is 0, 1, 2.

$R_{15}$ is as defined hereinabove and $R_{19}$ is hydrogen or lower alkyl. It is preferred that $R_{19}$ is hydrogen, and preferred values of $R_{15}$ are an electron donating group or hydrogen.

Preferred values of J are O or S(O)p; the preferred value of p is 1.

Preferred compounds of Formula VII have the formula:

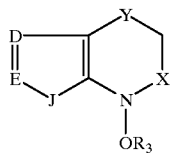

VIIa or N-oxides thereof wherein J, Y, $R_8$, $R_9$ n and $R_3$ are as defined hereinabove and X is C=O.

In compounds VII, VIII or VIIa as depicted above, it is preferred that at least one of D, E or J is a heteroatom. Furthermore, it is most preferred that at most two of J, E and D are heteroatoms. It is most preferred that only one of J, E and D is a heteroatom.

Preferred compounds have the formula:

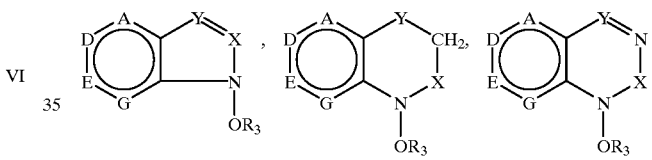

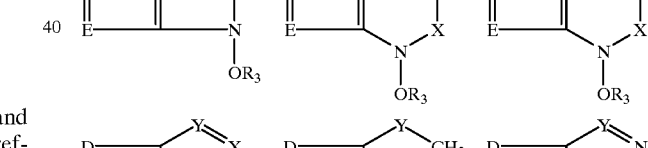

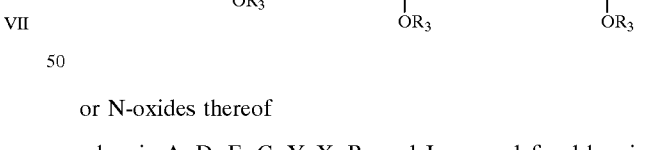

or N-oxides thereof wherein A, D, E, G, Y, X, $R_3$ and J are as defined hereinabove; and

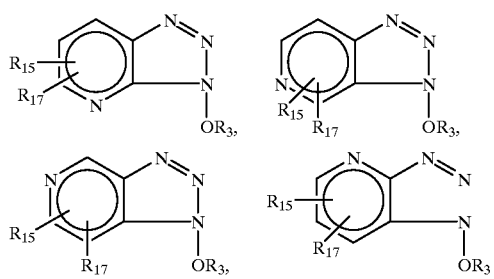

-continued

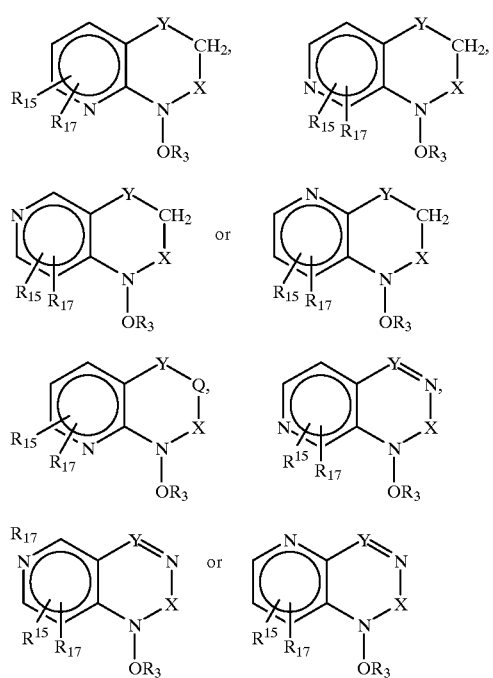

or N-oxides thereof.

Preferred embodiments of compounds of Formula II include

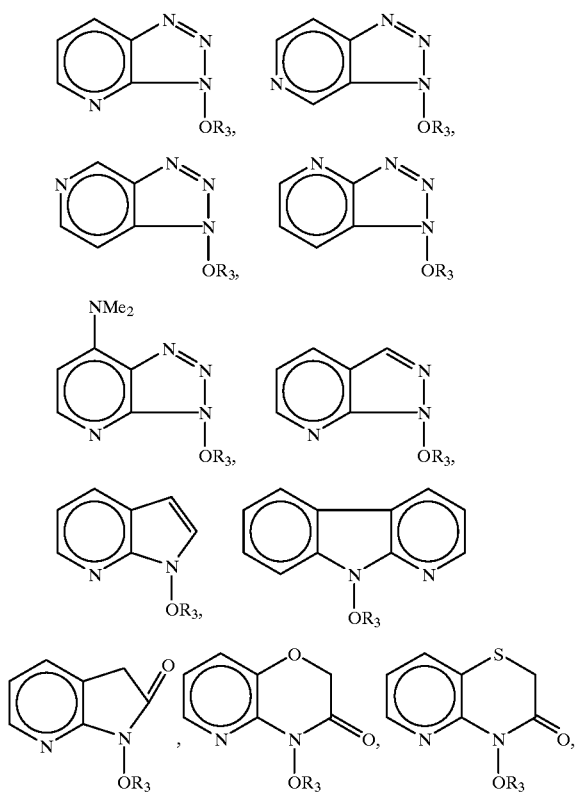

-continued

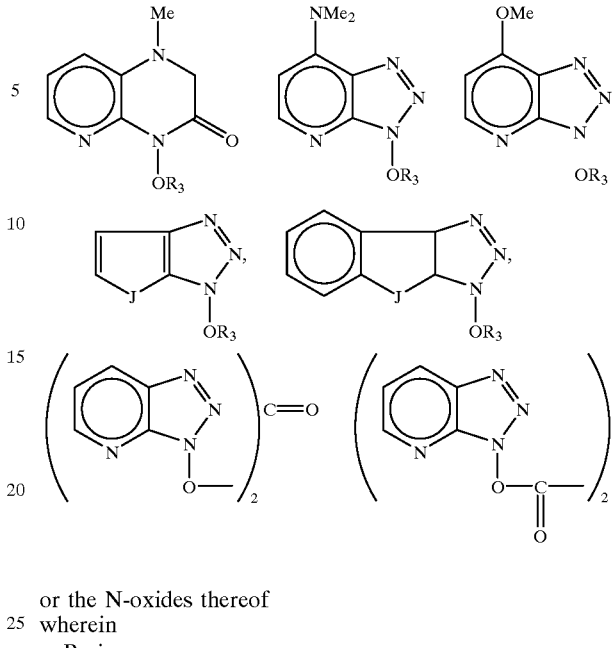

or the N-oxides thereof
wherein
R$_3$ is

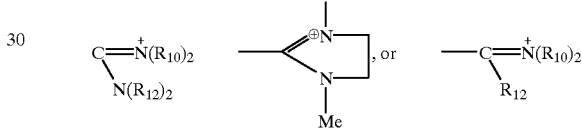

R$_{10}$ and R$_{12}$ are independently methyl, ethyl, propyl, butyl, pentyl CH$_2$CH$_2$O—CH$_2$CH$_3$,
R$_{15}$ is Me, Et, is—Pr, iPr$_2$N, or CMe$_3$
J is O, or S(O)p, and
p is 0, 1 or 2.

Of course, various combinations and permutations of the formulae described herein are also contemplated by the present invention. In addition, Markush groupings containing less than all of the elements described hereinabove as well as the various permutations thereof are also contemplated by the present invention.

These coupling agents of Formula II either are known compounds are prepared in accordance with the procedure described in U.S. Ser. No. 08/127,675, the contents of which are incorporated by reference.

Other coupling agents include the aryl fused compounds of the formula II

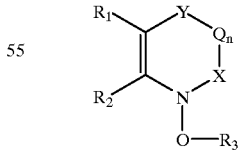

wherein Y, Q, N, and R$_3$ are as defined hereinabove, and R$_1$ and R$_2$ taken together with the carbon atoms to which they are attached form aryl groups. These compounds are prepared in a manner similar to that described for the compounds in U.S. Ser. No. 08/127,675.

Additionally, the term "coupling agent" includes the mixed anhydrides of N-α-amino protected amino acids. By definition an acid anhydride is a chemical compound derived from an acid by elimination of water. A mixed anhydride is a chemical compound derived from two different acids. As used herein, a mixed anhydride of an N-α-amino protected amino acid is the reaction product derived from the reaction of a N-α-amino protected amino acid and a hydrocarbyl- or hydrocarbyloxy carboxylic acid under sufficient conditions to eliminate water and to form an anhydride. It is to be noted that the anhydride is formed from the reaction of the α-carboxy group of the amino acid and the carboxy group of the carboxylic acid. A hydrocarbyl radical, as used herein, is a radical containing only hydrogen and carbon. It preferably contains 1–20 carbon atoms. Examples include alkyl, alkenyl, alkynyl, cycloalkyl, aryl, and the like. It is preferred that alkyl is lower alkyl, alkenyl and alkynyl each contain 2–6 carbon atoms, aryl is phenyl and cycloalkyl contains 5 or 6 ring carbon atoms. It is most preferred that the mixed anhydride is derived from the reaction of the N-α-amino protected amino acid and a carbonic acid or hydrocarbyl mono-ester of carbonic acid, especially lower-alkyl ester thereof, such as ethyl carbonic acid, isopropyl carbonic acid, sec-butyl carbonic acid, and the like. The most preferred hydrocarbyl esters of carbonic acid are alkyl esters, especially lower alkyl esters. It is also preferred that the mixed anhydride is derived from the reaction of the N-α-amino protected amino acid and the mono amide of carbonic acid, including the N-alkyl and the N,N-dialkyl derivatives thereof. In addition, it is preferred that the hydrocarbyl carboxylic group, is disubstituted on the α-carbon to the carboxy group. It is most preferred that the α-carbon is a tertiary carbon, e.g., pivalic acid (trimethylacetic acid), and the like.

Besides being a coupling agent, the mixed anhydride of N-α-amino protected amino acids especially the hydrocarbyl esters of carbonic acid also reacts directly with the ionic fluoride salt as defined hereinabove and can thus forms the N-α-amino protected amino acid fluoride in situ, which can then react with a carboxy protected amino acid or peptide as described herein.

In addition, the term coupling agents include the active esters, especially active esters of N- -protected amino acids. Examples include the N-hydroxy-piperidine esters of the N-α-protected amino acids, N-hydroxy succinimide esters of N-α-protected amino acids and the N-α-hydroxy phthalimide esters of N-α-amino protected amino acids and the like. It is to be noted that the esters are formed from the reaction of the -carboxy groups of the amino acids and the OH groups on the phthalimide, succinimide or piperidine compounds described above under esterifying conditions. These active agents and others are described in PROTECTIVE GROUPS in Organic Synthesis by J. W. Green, John Wiley & Sons, New York, 1981, pp. 180–184, the contents of which are incorporated by reference. In addition, also preferred are aryl esters of N- -amino protected amino acids, wherein the aryl group is unsubstituted and more preferably substituted with electron withdrawing groups. It is preferred that the aryl group is substituted by 1 to 5 electron withdrawing groups. The preferred aryl group is phenyl and preferred electron withdrawing groups are halo especially fluoro, nitro, alkanoyl, formyl, and the like. Examples of these active esters are the pentafluorophenyl ester of N-α-amino protected amino acid, nitrophenyl ester of N-α-amino protected amino acid and the like.

These esters are generated by reacting the arylol group, e.g., phenol, which is unsubstituted or substituted with electron withdrawing groups with the -carboxy group of the N-α-amino protected amino acid under esterifying conditions.

Another active ester is the ester of formula II, wherein Y, Q, X and n are as defined hereinabove, $R_1$ and $R_2$ taken together with the carbon atoms to which they are attached form an aryl or heteraryl ring wherein said heteraryl ring is an oxygen, sulfur or nitrogen containing heteroatom containing from 3 and up to a total of 13 ring carbon atoms said heteroaryl may be unsubstituted or substituted with lower alkyl or an electron donating group, and $R_3$ is $BLK_1$-$AA_1$.

$BLK_1$ is an amino protecting group and $AA_1$ is an amino acid less a hydrogen on the N-terminus and an OH on the C-terminus, i.e., $BLK_1$-AA is an N- -amino protected amino acid as defined herein. The preferred structures are again as defined by structures IIA–VIII as defined hereinabove and the other preferred embodiments as described hereinabove, except that $R_3$ is $BLK_1$-$AA_1$.

However, as with the mixed anhydride, the active esters also react directly with the ionic fluoride salt as defined herein and thus form the N-α-amino protected amino acid fluoride in situ which can then react with a carboxy protected amino acid or peptide, as described herein.

Preferred coupling agents are DCC, DIC, O-benzotriazolyl-1-yl-1,1,3,3-tetramethyluronium hexafluorophosphate(HBTU), O-(7-azabenzotriazol-1-yl-1,1,3,3-tetramethyluronium hexafluorophosphate (HATU); O-(7-azabenzotriazol-1-yl-1,1,3,3-bis (tetramethylene uronium hexafluorphosphate (HApyU), O-(7-azabenzotriazol-1-yl)-1,1,3,3-bis (pentamethylene) uronium hexafluorophosphate (HApipU),O-(7-azabenzotrizol-1-yl)-1,3-dimethyl-1,3-trimethylene uronium hexafluorophosphate (HAMTU), benzotriazolyl-yl-1,1,3,3-bis (tetramethylene uronium tetrafluoroborate)(TBTU), TFFH, mixed anhydrides, EZDQ, active esters, such as pentafluorophenyl or succinimide esters of N-α-amino protected amino acid, and the like.

The ionic fluoride salts are salts containing a cation and an anion. The anion portion of the salt is the portion of the salt that is involved in the reaction for forming the amino acid fluoride. As such, it contains at least one ionizable fluoride, i.e., a fluoride ion that dissociates from the salt when placed in aqueous solution. Preferred anions have the formula given herein above:

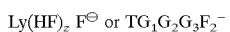

wherein
  z is 0–10;
  y is 0 or 1;
  L is $TG_1G_2G_3G_4$;
  T is a Group IV element consisting of Si, Ge, Sn or Pb; and
  $G_1$, $G_2$, $G_3$ and $G_4$ are independently halogen, hydrogen, alkyl, aryl, arylalkyl, cycloalkyl or cycloalkyl alkyl.

The preferred value of Z is 0–4. It is preferred that $G_1$, $G_2$, $G_3$ and $G_4$ are alkyl, aryl, or arylalkyl. It is preferred that T is Sn or Si.

Although the cation portion is a spectator ion and is not involved in the overall reaction, certain cations are preferred. They include the alkali metals, the alkaline earth metals, hydrogen cation, ammonium ($NH_4+$), $NQ_5Q_6Q_7Q_8+$, $PQ_5Q_6Q_7Q_8+$, $SQ_5Q_6Q_7+$, $HalQ_5Q_{6+}$, or

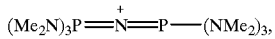

wherein
  $Q_5$, $Q_6$, $Q_7$ and $Q_8$ are independently hydrogen, lower alkyl, aryl, or aryl lower alkyl, Hal is halo, such as iodo, bromo, or chloro.

It is preferred that Q5 is arylalkyl, especially benzyl and Q6, Q7 and Q8 are aryl, especially phenyl.

Preferred examples of ionic fluoride salts include $(C_6H_5)_4 P^{\oplus}H_2F_3^{\ominus}$, n $Bu_4N^{\oplus}$ $(C_6H_5)_3$ $SnF_2^{\ominus}$, benzyltriphenylphosphonium dihydrogen trifluoride, i.e., $[(BTPP)H_2F_3]$, n-$Bu_4N^{\oplus}(C_6H_5)_3$ $SnF_2^{\ominus}$, $Et_4N^{\oplus}F^{\ominus}$, $Me_4N^{\oplus}F^{\ominus}$, $Et_2NSF_3$, $(Me_2N)_3S^{\oplus}$ $Me_3SiF_2^{\ominus}$, $Bu_4N^{\oplus}F^{\ominus}$, $Bu_4N^{\oplus}HF_2^{\ominus}$, $Me_3S^{\oplus}F^{\ominus}$, $Bu_4P^{\oplus}F^{\ominus}$, $Bu_4P^{\oplus}HF_2^{\ominus}$, $Bu_4P^{\oplus}H_2F_3^{\ominus}$, hexadecyl $N^{\oplus}Me_3F^{\ominus}$, hexadecyl $N^{\oplus}Me_3$ $HF_2^{\ominus}$, hexadecyl $NMe_3^{\oplus}HF_3^{\ominus}$, $(C_6H_5)_4P^{\oplus}F^{\ominus}$, $(C_6H_5)_4P^{\oplus}HF_2^{\ominus}$, $(C_6H_5)_4P^{\oplus}H_2F_3^{\ominus}$, $(C_8H_{17})_4N^{\oplus}F^{\ominus}$, $(C_8H_{17})_4N^{\oplus}HF_2^{-}$, $(C_8H_{17})_4$ $P^{\oplus}H_2F_3^{\ominus}$, $(Me_2N)_3P=N^{\oplus}=P(NMe_2)_3$ $F^{\ominus}$, $BuNMe_3$ $F^{\ominus}$, $KF(HF)z_1$, $z_1=0, 1, 2, 3$ or 4
$CsF(HF)z_1$, $z_1=0, 1, 2, 3$, or 4
$NaF(HF)z_1$, $z_1=0, 1, 2, 3$, or 4
$NaF(HF)z_1$, $z_1=0, 1, 2, 3$, or 4

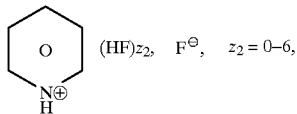

polyvinyl pyridine$(HF)z_3$, $z_3=1–7$,
polyethylene —$CH_2N^{\oplus}Me_3^{\ominus}F^{\oplus}$,

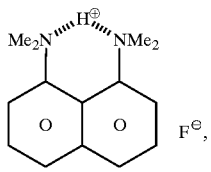

$Et_3NH^{\oplus}(HF)$ $z_4F^{\ominus}$, wherein $z_4=1–3$, $H_2SiF_6$ and the like.

The ionic fluoride salts are either known compounds or are prepared by art recognized techniques. Their synthesis is exemplified by the synthesis of benzyltriphenyl phosphonium dihydrogen-trifluoride. In this case, an excess of the fluoride salt, e.g., $KHF_2$, is reacted with a halo salt, $(PQ_5Q_6Q_7Q_8$ Hal, i.e., where P, $Q_5$, $Q_6$, $Q_7$ and $Q_8$ are defined above and Hal is Bromo, Chloro or Iodo) e.g., benzyltriphenylphosphonium chloride. The reaction is effected in a solvent which will dissolve both reagents and the product, such as water and the desired product is separated therefrom. This reaction may be effected at temperatures above the freezing point of the solvent (e.g., water) and up to the boiling point thereof, but preferably it is performed at room temperature.

As used herein, the term "alkyl", when used alone or in combination with other groups, refers to a carbon chain containing from one to twenty carbon atoms. It may be a straight chain or branched and includes such groups as methyl, ethyl, propyl, isopropyl, n-pentyl, amyl, hexyl, heptyl, octyl, nonyl, decyl, pentadecyl, hexadecyl, and the like. The preferred alkyl groups are lower alkyl groups containing 1–6 carbon atoms. It is even more preferred that alkyl contains from 1–3 carbon atoms. It is most preferably methyl.

The term "aryl" as used herein, alone or in combination, refers to an aromatic ring system containing from 6–10 ring carbon atoms and up to a total of 15 carbon atoms. It includes such groups as phenyl, α-naphthyl, β-naphthyl, and the like.

"Aralkyl groups" are alkyl groups attached to the aryl group through an alkylene bridge. Such groups include phenethyl, phenpropyl and most preferably benzyl.

"Cycloalkyl" as used herein refers to a cycloalkyl group containing only ring carbon atoms and from 3–10 ring carbon atoms and up to a total of 15 carbon atoms. It may consist of 1 ring or two fused rings or three fused rings. Examples include cyclopropyl, cyclobutyl, cyclopentyl, cyclohexyl, cycloheptyl, cyclooctyl, cyclononyl, decalinyl, norbornyl, adamanty and the like.

"Cycloalkylalkyl" denotes alkyl groups attached to the cycloalkyl group through an alkylene bridge. Such groups include cyclohexylmethyl, cyclopentylethyl, and the like.

Unless indicated to the contrary, halogen, as used herein refers to fluorine, chlorine, bromine or iodine.

As employed herein, the term "heteroaryl" is a heteroaromatic containing at least one heteroatom ring atom selected from nitrogen, sulfur and oxygen and up to a maximum of four ring heteroatoms. The heteroaryl group contains from 5 to 14 ring atoms and up to a total of 13 ring carbon atoms and a total of 18 carbon atoms. The heteroaryl group may be monocyclic, bicyclic or tricyclic. Also included in this expression are the benzoheteroaromatic.

The heteroaryl group preferably contains no more than two ring heteroatoms, and most preferably contains one ring heteroatom. The most preferred ring heteroatoms are oxygen and nitrogen, with nitrogen being the most preferred.

If nitrogen is a ring atom, N-oxides can also be formed. The present invention contemplates the N-oxides of the nitrogen containing heteroaryls.

Examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, isothiazolyl, isoxazolyl and the like. It is preferred that the heteroaryl group is pyridyl, pyrrolyl, furyl, indolyl, quninolyl, isoquinolyl or benzofuryl. Especially preferred is pyridyl.

Alkyl carbonyl refers to an alkyl group attached to the main chain through a carbonyl. Similarly, aryl carbonyl refers to an aryl group attached to the main chain through a carbonyl group.

As used herein, an "electron donating group" shall designate a group that will release or donate electrons more than hydrogen would if it occupied the same position in the molecule. See J. March, *Advanced Organic Chemistry*, 3rd Ed., John Wiley & Sons p. 238 (1985). These types of groups are well known in the art. Examples include lower alkylamino, diloweralkylamino, amino, halo, aryl, lower alkoxy, hydroxy, lower aralkoxy, aryloxy, mercapto, lower alkylthio, and the like. The preferred electron donating groups are amino, hydroxy, lower alkoxy, lower alkylamino and diloweralkylamino.

The presence of all three elements, i.e., the ionic fluoride salt, the coupling agent, and the N-α-amino protected amino acid or acylating derivative thereof are required for the in situ preparation of the N-α-amino protected amino acid fluoride. The reaction is effected by mixing the three elements in a suitable solvent in which the amino acid or acylating derivative thereof, the ionic fluoride salt and the coupling agent and the resulting amino acid fluoride are soluble, or are partially soluble. Examples of suitable solvents include dimethylformamide, methylene chloride (DCM), N,N-dimethylpyrrolidine (NMP), THF, ethyl ether, dioxane, and the like. DMF and DCM are the preferred solvents. The reaction may be effected at temperatures ranging from about 0° C. to the reflux temperature of the solvent, but it is preferred that the reaction be effected at about room temperature.

Effective amounts of the fluoride additive, the coupling agent and the N-α-amino protected amino acid or acylating derivative thereof are used to form the N-α-amino protected amino acid fluoride in situ. Preferably the ratio of ionic fluoride salt to amino acid ranges from about 1:5 to about 5:1 equivalents, and more preferably from about 1:1 to about 5:1 equivalents, respectively, and most preferably, the ratio is about 1:1 equivalents. Similarly, the ratio of coupling agent to amino acid ranges from about 1:5 to about 5:1 equivalents, and more preferably from about 1:1 to about 5:1, respectively and most preferably the ratio is about 1:1. Finally, it is preferred that the ratio of ionic fluoride salt to coupling agent ranges from about 1:10 to about 10:1 equivalents, and more preferably from about 1:5 to about 5:1 equivalents, respectively and the ratio is most preferably about 1:1 equivalents. In fact, it is most preferred that the equivalent ratio of amino acid: fluoride salt: coupling reagent is about 1:1:1.

The amino acid fluoride thus formed, in situ, is produced without racemization. In other words, the L amino acid would produce the L-amino acid fluoride. Similarly, the D-amino acid fluoride would be prepared from the corresponding D-amino acid.

favorable solvation properties of each. The reaction takes place under mild conditions usually ranging from about 0° C. to about 30° C. After the peptide is formed, the blocking groups are removed by techniques known to one skilled in the art.

The process described herein with the formation of the N-α-amino protected amino acid fluoride in situ followed by the coupling reaction described hereinabove, is applicable in both solution phase and solid phase synthesis. The synthesis of higher peptides according to the present invention is effected by constantly repeating the following sequence of steps:

1) formation of an amino acid fluoride in situ by reacting the appropriate amino acid or acylating derivative thereof, a coupling agent and the ionic fluoride salt;
2) reacting the amino acid fluoride produced in situ with a second amino acid having a free amino group and protected a carboxy group or peptide having a free amino group, and a protected carboxyl group to form a peptide bond; and
3) removal of the protecting groups By repeating steps 1–3, higher peptides are formed. This is clearly shown by the following sequence:

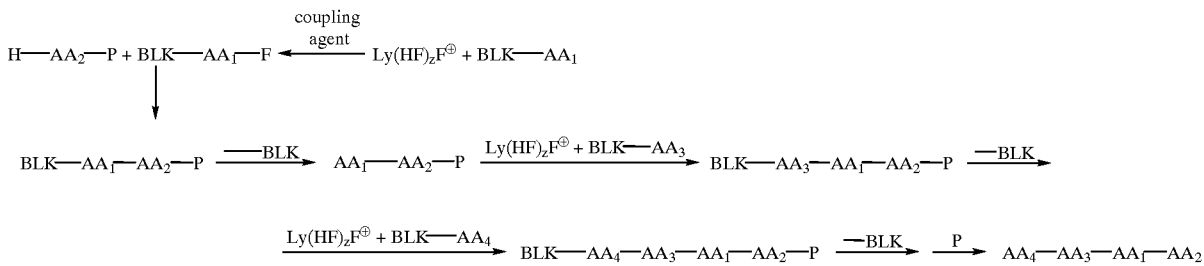

The amino acid fluoride thus formed can then react with an amino acid having a free α-amino group or peptide having a free α-amino group to produce a protected peptide in accordance with standard techniques known in the art. Removal of the protecting groups affords the desired peptide.

This process can be repeated to form tripeptides, tetrapeptides, or higher peptides until the desired product is attained. The scope of the present process is broad, as the amino acid fluorides prepared in accordance with the first step can be coupled with an amino acid, dipeptide, tripeptide, or higher peptide, as long as it has a free α-amino group.

Inasmuch as the amino acid fluoride prepared in accordance with the present invention is formed in situ, it reacts immediately with the peptide or amino acid having a free amino group already present in the reaction mixture. Thus, another aspect of the present invention is the preparation of peptides. Effective amounts of the amino acid fluoride formed in situ is reacted with the amino acid or peptide having a free α-amino group. Preferably, the equivalent ratio of amino acid fluoride to the amino acid peptide having a free amino group ranges from about 1:1 to about 10:1, respectively, and most preferably from about 2:1 to about 4:1.

The coupling reaction usually takes place in an inert organic solvent such as dimethylformamide (DMF), methylene chloride (DCM), N-methylpyrrolidine (NMP), ethyl ether, THF, dioxane, or the like. In fact, DMF, or DCM is the preferred solvent in solid phase synthesis because of the In the above scheme, Ly, and z are as defined hereinabove, and $AA_1$, $AA_2$, $AA_3$, and $AA_4$ are independently N-α-amino protected amino acid. BLK is a α-amino blocking group, and P is a peptidyl-resin in solid phase synthesis or a carboxy protecting group commonly used in solution peptide synthesis, such as the methyl ester, t-butylester, β-trimethylsilyethyl, benzyl ester, and the like. A variety of carboxy protecting groups known in the art may be employed. Examples of many of these possible groups can be found in "Protective groups in Organic Synthesis", by T. W. Green, John Wiley and Sons, 1981, the contents of which are incorporated by reference.

In the above sequence, the ionic fluoride salt was represented by $Ly(HF)zF^{\ominus}$. However, this was just exemplary as the above sequence of steps could be effected if the anion of the ionic fluoride salt were $TG_1G_2G_3F_2^-$.

As shown by the above scheme, the N-α-amino protected amino acid is reacted with an ionic fluoride salt, and a coupling agent to form an N-α-amino protected amino acid fluoride in situ which is reacted with a second amino acid in which the carboxy group is protected and which has a free amino group. A peptide is formed between the first amino acid and the second amino acid. The peptide chain can be increased by removing the α-amino protecting group by techniques known to one skilled in the art. Another N-α-amino protected amino acid fluoride is formed in situ in accordance with the present invention and this is 3reacted with the dipeptide formed hereinabove to produce the N-α-amino protected tripeptide. The N-α-amino protecting group of the tripeptide is removed and the above cycle is repeated until the desired peptide has been obtained. In the very last step the protecting groups, i.e., the N-α-amino protecting group, the α-carboxy protecting group and the protecting groups on the side chains, if any, are removed.

The present invention can readily be utilized in solid phase peptide synthesis. Solid phase peptide synthesis is based on the stepwise assembly of a peptide chain while it is attached at one end to a solid support or solid phase peptide resin. Two methods are generally well known in the art.

One, the Merrifield method, employs a solid support for attachment of the amino acid or peptide residues. This method employs N-protected amino acids as building blocks which are added to an amino acid or peptide residue attached to the solid support at the acyl (acid) end of the molecule. After the peptide bond has been formed, the protected group is removed and the cycle repeated. When a peptide having the desired sequence has been synthesized, it is then removed from the support.

The second method, the inverse Merrifield method, employs reagents attached to solid supports in a series of columns. The amino acid or peptide residue is passed through these columns in a series to form the desired amino acid sequence.

These methods are well known in the art as discussed in U.S. Pat. Nos. 4,108,846, 3,839,396, 3,835,175, 4,508,657, 4,623,484, 4,575,541, 4,581,167, 4,394,519 as well as in *Advances in Enzymology*, 32,221 (1961) and in PEPTIDES, Vol, 2, edited by Erhard Gross and Johannes Meienhoffer, Academic Press, New York, N.Y. pp. 3–255 (1980) and all of these are incorporated herein by reference as if fully set forth herein.

One of the surprising results accompanying the preparation of peptides utilizing the in situ preparation of amino acid fluoride of the present invention is the higher yields of peptide product that is formed as compared when the ionic fluoride salt is not present. Without wishing to be bound, it is believed that this phenomenon can be explained by comparing the mechanism of action in the absence and presence of ionic fluoride salt.

In the absence of ionic fluoride salt, the reaction between the coupling agent and the amino acid can proceed via several different pathways, some of which leads to by-products. This is illustrated in the following scheme, wherein $T_1N=C=NT_1$ represents an exemplary coupling agent (e.g., carbodiimides wherein $T_1$ may be alkyl or cycloalkyl), $UCO_2H$ represents a first amino acid with a free carboxy group and $VNH_2$ represents a second amino acid with a free amino group:

SCHEME I

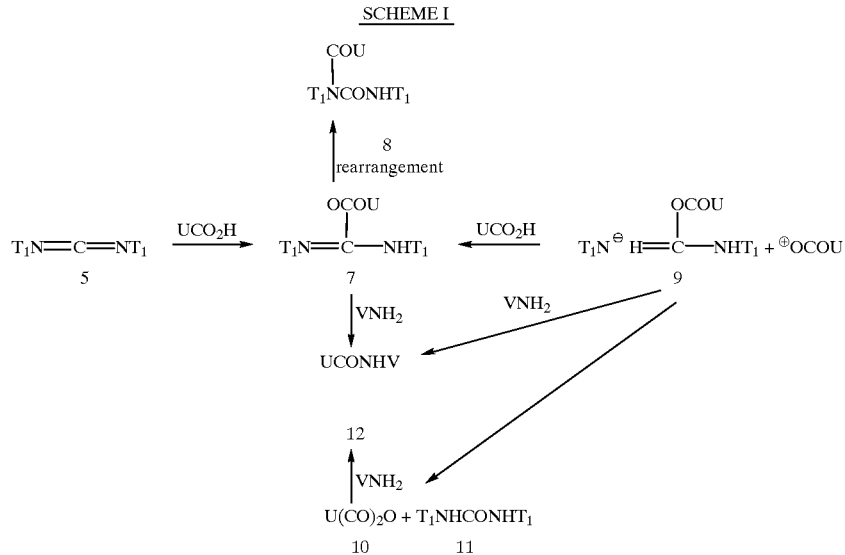

The final product, amide 12, can be derived from the unstable O-acylurea 7, its protonated form 9 or the symmetric anhydride 10 which is derived from 9 by reaction with the acid anion. Formation of the rearrangement product 8 represents loss of active material since this reaction is irreversible. In the presence of fluoride ionic salt, active intermediate 7 is diverted to give the acid fluoride, thus accounting for the excellent results obtained in the work described here (Scheme II).

SCHEME II

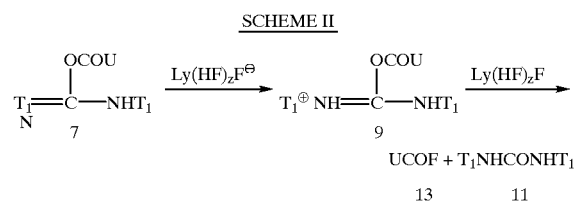

Under optimum conditions, all of the acid is converted to the acid fluoride, thus serving to guarantee an efficient coupling process as the acid fluoride reacts with the amino component of the amino acid. It is believed to be a direct process without the multiple pathway steps believed to be present when the ionic fluoride salt is absent. Therefore, the process is more efficient in the presence of the ionic fluoride salt.

Moreover, by the in situ process of the present invention, amino acid fluorides can be prepared which heretofore, could not be prepared. For example, as shown hereinbelow, FMOC—His(Trt)—F can be prepared without significant racemization.

Another aspect of the present invention is directed to a kit comprising the three elements described hereinabove for forming the amino acid fluoride in situ. More specifically, this aspect of the invention is directed to a kit comprising in a first compartment an N-α-amino protected amino acid or acylating derivative thereof, in a second compartment a coupling agent and in a third compartment an ionic fluoride salt as described herein. A variation thereof is a kit comprising two compartments, wherein the first compartment contains the ionic fluoride salt of the present invention admixed with the N-α-amino protected amino acid or acylating derivative thereof and a second compartment containing the coupling agent. Thus, when ready for use the amino acid, the coupling agent and the ionic fluoride salt are removed from each compartment and mixed together with an amino acid or peptide having a free amino group in the appropriate solvent, thereby generating a peptide from the in situ formed N-α-amino protected amino acid fluoride.

Another variation is a kit comprising any two of the elements described hereinabove. More specifically, a variation is directed to a kit comprising in a first compartment the ionic fluoride salt as described hereinabove and in a second compartment the N-α-amino protected amino acid. Alternatively, the kit contains 1 compartment containing the N-α-amino protected amino acid admixed with the ionic fluoride salt. Alternatively, a kit is comprised of two compartments, one compartment containing the ionic fluoride salt and the second compartment containing the coupling agent.

Thus, when these latter kits are ready for use, the ionic fluoride salt and either the N-α-amino protected amino acid or coupling agent is mixed in solution containing the third element (i.e., the coupling agent or the N-α-amino protected amino acid, respectively) and an amino acid or peptide having a free amino group to generate the desired peptide.

It is to be noted that the in situ process described hereinabove is not limited to the preparation of amino acid fluorides in situ. The coupling agent and the ionic fluoride salt can be reacted with an organic carboxylic acid especially hydrocarbyl organic acids, to form the corresponding organic carboxylic acid fluoride in situ.

Another aspect of the present invention is directed to novel ionic fluoride salts. The ionic fluoride salts described herein generally have the formula:

Cat—Ani wherein

Cat is an alkali metal cation, alkaline earth metal cation, hydrogen cation, $NH_4+$, $NQ_5Q_6Q_7Q_8^{\oplus}$, $PQ_5Q_6Q_7Q_8^{\oplus}$, $SQ_5Q_6Q_7^{\oplus}$, $Hal\ Q_5Q_6^{\oplus}$ or $(Me_2)N_3\ P{=}N{=}P{-}N(Me_2)_3$ and Ani is a fluoride salt anion of the formula:

$Ly(HF)_zF^{\ominus}$ or $TG_1G_2G_3F_2^{\ominus}$ wherein $Q_5$, $Q_6$, $Q_7$, $Q_8$, Hal, Ly, z, T, $G_1$, $G_2$, $G_3$, $G_4$ are as defined herein.

It is preferred that $Q_5$ is arylalkyl and $Q_6$, $Q_7$ and $Q_8$ are aryl, especially phenyl.

It is to be understood, unless indicated to the contrary, that the aryl, aryl alkyl groups, alkyl groups, cycloalkyl group, cycloalkyl alkyl groups and the other groups defined herein may be unsubstituted or substituted with an electron donating group or electron withdrawing groups, including alkyl groups, which do not interfere with the reaction for forming the amino acid fluoride or the coupling reaction, described herein.

The invention will now be illustrated by examples. The examples are not intended to be limiting of the scope of the present invention. In conjunction with the general and detailed descriptions above, the examples provide further understanding of the present invention:

EXAMPLE 1

Benzyltriphenylphosphonium Dihydrogentrifluoride

A solution of 7.8 g (20 mmol) benzyltriphenylphosphonium chloride in 100 ml of $CH_2Cl_2$ was stirred vigorously with a solution of 78.2 g (1 mole) of $KHF_2$ in 200 ml of distilled water for 0.5 h in a plastic flask. After separation of layers, the organic layer was stirred two more times as indicated above with fresh 200-mL portions of $KHF_2$ solution. Finally, the organic layer was separated and the solvent removed in vacuum. The solid residue upon recrystallization from methanol-ether gave a colorless crystalline mass (8.16 g, yield 99%), mp 148–150° C.; $^1H$ NMR ($CDCl_3$); δ 4.85 (d, 2, $CH_2$); 7.0–7.7 (m, 22); Anal. Calcd for $C_{25}H_{24}PF_3$; C, 72.80; H, 5.86; F, 13.82. Found: C, 72.95; H, 5.80; F, 13.60.

EXAMPLES 2–4

Manual Solid Phase Synthesis

In Examples 2–4, the following syntheses of peptides were utilized. All syntheses were carried out in 5- or 10-mL plastic syringes using a PAL-PEG-PS resin using either 4 or 5 eqs. excess amino acid, deblocking times of 7 min. and coupling times of 30 min. Preactivation via DCC or DIC was carried out in some cases in $CH_2Cl_2$ followed by evaporation of solvent and transfer to DMF for coupling. In other cases DMF was used for both activation and coupling. Parallel runs with and without additive were carried out side-by-side.

For non-carbodiimide coupling reagents, e.g., TFFH, HATU and TBTU, parallel runs were made similarly in the absence and presence of ionic fluoride salt. Co-injection experiments confirmed that the presence of fluoride salt always guaranteed the best result.

EXAMPLE 2

H—Tyr—Aib—Aib—Phe—Leu—$NH_2$

Using the above procedure, and various coupling agents in the presence and absence of ionic fluoride salts, the above pentapeptide was prepared and the results compared. The data is tabulated in Table 1.

TABLE 1

H-Tyr-Aib-Aib-Phe-Leu-NH$_2$[a]

| Solvent | Coupling Reagent | Base[b] | Proactivation Time, min. | ionic fluoride salt | Yield (%) | des-Aib-4-mer(%) |
|---|---|---|---|---|---|---|
| DMF | HATU/HOAT | DIEA(2) | 7 | — | 25 | 60.5 |
| DMF | HATU | DIEA(2) | 7 | — | 83.4 | 4.5 |
| DMF | TFFH | DIEA(2) | 7 | — | 87.1 | 9.0 |
| CH$_2$Cl$_2$/DMF[c] | DCC | DIEA(1) | 7 | — | 50.6 | 58.8 |
| CH$_2$Cl$_2$/DMF[c] | DCC | — | 7 | — | 90.3 | 73.5 |
| CH$_2$Cl$_2$/DMF[c] | DCC | — | 7 | (C$_6$H$_5$)$_4$PH$_2$F$_3$ | 97.8 | 10.5 |
| DMF | TFFH | DIEA(2) | 7 | (C$_6$H$_5$)$_4$PH$_2$F$_3$ | 71.2 | 7.1 |
| DMF | DCC | — | 7 | (C$_6$H$_5$)$_4$PH$_2$F$_3$ | 60.4 | 55.4 |
| DMF | DIC | — | 15 | — | 32.2 | 78.1 |
| DMF | DIC | — | 15 | (C$_6$H$_5$)$_4$PH$_2$F$_3$ | 67.9 | 18.8 |
| DMF | DIC | — | 15 | TsOH | 75.9 | 26.5 |
| DMF | DIC | — | 15 | nBu$_4$N(+)(C$_6$H$_5$)$_3$SnF$_2$(−) | 40.8 | 49.1 |

[a]Manual syntheses; a 5-fold excess of the Fmoc amino acid was used with a coupling time of 30 min (single).
[b]The number of equivalents per equivalent of acid is given in parenthesis.
[c]In these cases the preactivation was carried out in CH$_2$Cl$_2$ and the solvent evaporated so that the coupling reaction was carried out in DMF.

It should be noted that the pentapeptide 14

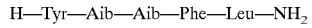

14 gives via manual solid phase synthesis using DCC alone mainly the corresponding tetrapeptide 15

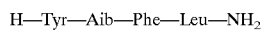

15 due to the extreme difficulty of the Aib-Aib coupling step. The ratio of desired-to undesired peptide is 0.36. In contrast, in the presence of tetraphenylphosphonium dihydrogen trifluoride (TPP$^{(+)}$H$_2$F$_3$$^{(-)}$) the desired pentapeptide 14 is obtained in a yield of 97.8% with a purity of crude product of 90% (ratio of desired to undesired, 8.44). For this synthesis, the standard method of preactivating in DCM (methylene chloride) solvent followed by evaporation and coupling in DMF solution was followed. Direct preactivation in DMF can be speeded up by the presence of a catalytic amount of a strong sulfonic acid. For comparison data on the synthesis of pentapeptide 14, see Table 1.

Infrared studies in CH$_2$Cl$_2$ and DMF which allowed one to follow formation of the acid fluoride, symmetric anhydride and oxazolone as well as conversion of the last named acid fluoride were made under various conditions. As an α,α-disubstituted amino acid Fmoc—Aib—OH 16 is readily converted to an oxazolone 17 so that initially a mixture of acid fluoride, symmetric anhydride, and oxazolone is formed (eq.5).

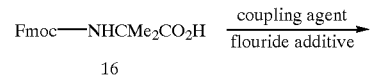

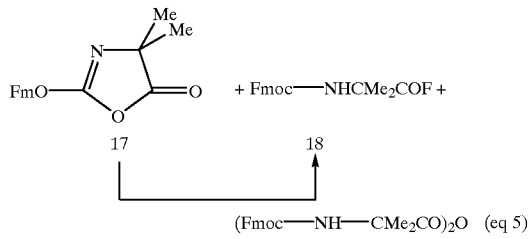

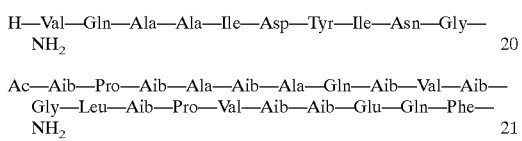

Depending on the conditions 17 is converted more or less readily to acid fluoride 18. Model studies showed that conversion of anhydride 19 to acid fluoride was slow and incomplete so that for practical purposes it is important that the conditions be such that anhydride is by-passed. This result is achieved by having the fluoride ionic salt present from the start of the reaction. The speed and extent of formation of 18 determines the overall ease of peptide bond formation.

EXAMPLE 3

Using the methodology indicated hereinabove, the following peptides were prepared:

H—Val—Gln—Ala—Ala—Ile—Asp—Tyr—Ile—Asn—Gly—NH$_2$    20

Ac—Aib—Pro—Aib—Ala—Aib—Ala—Gln—Aib—Val—Aib—Gly—Leu—Aib—Pro—Val—Aib—Aib—Glu—Gln—Phe—NH$_2$    21

The results showed that for ACP (65–74) 20 a manual solid phase synthesis using DIC (preactivation for 7 min. in CH$_2$Cl$_2$, evaporation of the solvent and dissolution of the residue in DMF) gave an excellent crude product. If base (DIEA) was added to the coupling step the crude peptide was of lesser quality. With eight Aib residues and one Aib—Aib unit, peptide 21 represents a difficult challenge for solid phase assembly. Previously only acid fluorides were successful in the solid phase synthesis of this model. Now the present method is also shown to be successful.

EXAMPLE 4

Syntheses were also carried out on the ACP decapeptide which had been modified by substituting α-methylalanine (Aib) for the two alanine units. As a general model this peptide 22 is quite

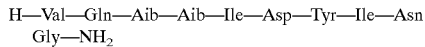

22 demanding yet is only half the size of alamethicin amide 21, allowing two test syntheses to be completed during the same time period.

With this new model available a number of other coupling systems have been examined in order to extend the generality of the ionic fluoride salt. For example, TBTU by itself provided only a small amount of the desired decapeptide 22; the main product being the des-Aib analog. On the other hand, TBTU in the presence of $BTPPH_2F_3$ gave peptide 22 as the only major product. Similarly while results with HATU were better than with TBTU since a 50—50 mixture of the desired peptide and the des-Aib peptide was obtained, the use of HATU along with the ionic fluoride salt gave only the desired peptide. It is thus to be emphasized that use of TBTU with ionic fluoride salt, in accordance with the present invention, can equal or better the results obtained via HATU.

In the case of TFFH, results with and without ionic fluoride salt were nearly the same in terms of peptide quality, although the yield increased from 52% to 81% when the ionic fluoride salt was used. Other inexpensive coupling reagents can be similarly modified to bring their coupling level up to that of acid fluorides which are currently the most efficient of the common coupling species. This includes the use of EDC, active esters of various kinds, mixed anhydrides, EEDQ, NCAs, (N-carboxyanhydrides), ethoxyacetylene, yneamines, ketene imines, and the like.

The following experiments clearly further illustrate that the presence of the ionic fluoride salts of the present invention provide a protective a effect against racemization.

EXAMPLE 5

FMOC—Leu—Pro—$NH_2$

1. Flowsheet.

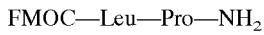

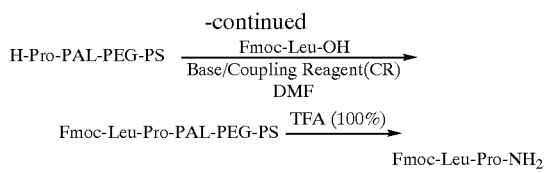

2. Conditions.

Fmoc—Pro—PAL—PEG—PS (0.2 mmol/g), 100 mg.

* Fmoc—Leu—OH, 3 eqs. excess, 0.06 mmol, 21.2 mg.

* Base, 6 eqs. excess-see Table 2.

* CR, 3 eqs. excess-see Table 2.

* Fluoride salt, 3 eqs. excess, 24.7 mg-see Table 2.

* Solvent: DMF (0.4 mL). Coupling time: 30 min.

*The asterisk identifies the components of the preactivation solution. For preactivation times see Table 2.

3. General Procedure.

In 5-mL syringe tubes fitted at the bottom with a Teflon frit was weighed 100 mg of Fmoc—Pro—PAL—PEG—PS (0.2 mmol/g). The resin was washed with DMF (5×5 mL), treated with 20% piperidine in DMF (4 mL) for 7 min and then washed with DMF (5×5 mL). After removing the solvent by water aspirator vacuum the preactivated solution (see above and Table 2) was added to the resin. During the 30 min coupling time the resin was stirred from time-to-time with a Teflon stick. At the end of 30 min the resin was washed with DMF (5×5 mL), $CH_2Cl_2$ (5×5 mL), EtOH (1×5 mL), ether (2×5 mL) and dried in vacuo for 0.5 h. The dry resin was treated with 2 mL of 100% trifluoroacetic acid (TFA) for 1 h. The TFA was removed by filtration into a collection vessel and the resin washed on the filter with $CH_2Cl_2$ (2×5 mL). The combined filtrates were concentrated in vacuo at room temperature to dryness and the residue dissolved in 1 mL of $CH_3CN$ for analysis by direct injection onto an HPLC column.

4. HPLC Separation.

Column: Nova Pak, 4μ, $C_{18}$.

Solvent system: isocratic, 40% $CH_3CN$ (0.1% TFA)—60% $H_2O$ (0.1% TFA).

Flow rate: 1 mL/min.

Detector: PDA at 220 nm.

The results are given in Table 2.

TABLE 2

System: Fmoc-Leu-OH + H-Pro-PAL-PEG-PS, with or without the Universal Fluoride Salt $(C_6H_5CH_2P(C_6H_5)_3^{\oplus}H_2F_3^{\ominus})$

| CR(amt.) | Base(amt.) | Additive | Preactiv. time(min) | DL(%) |
| --- | --- | --- | --- | --- |
| HATU(22.8 mg) | DIEA(20.9 μL) | − | 1 | 0.96 |
| HATU(22.8 mg) | DIEA(20.9 μL) | + | 1 | 0.81 |
| HATU(22.8 mg) | DIEA(20.9 μL) | − | 7 | 0.81 |
| HATU(22.8 mg) | DIEA(20.0 μL) | + | 7 | 0.82 |
| HATU(22.8 mg) | TMP**(15.9 μL) | − | 7 | 0.22 |
| HATU(22.8 mg) | TMP(15.9 μL) | + | 7 | 0.33 |

TABLE 2-continued

System: Fmoc-Leu-OH + H-Pro-PAL-PEG-PS, with or without the Universal Fluoride Salt $(C_6H_5CH_2P(C_6H_5)_3^{\oplus}H_2F_3^{\ominus})$

| CR(amt.) | Base(amt.) | Additive | Preactiv. time(min) | DL(%) |
|---|---|---|---|---|
| TBTU(19.2 mg) | DIEA(20.9 μL) | − | 1 | 0.82 |
| TBTU(19.2 mg) | DIEA(20.9 μL) | + | 1 | 0.79 |
| TBTU(19.2 mg) | DIEA(20.9 μL) | − | 7 | 0.85 |
| TBTU(19.2 mg) | DIEA(20.9 μL) | + | 7 | 0.76 |
| TBTU(19.2 mg) | TMP(15.9 μL) | − | 7 | 0.26 |
| TBTU(19.2 mg) | TMP(15.9 μL) | + | 7 | 0.24 |
| TFFH(15.9 mg) | DIEA(20.9 μL) | − | 7 | 0.78 |
| TFFH(15.9 mg) | DIEA(20.9 μL) | + | 7 | 0.74 |
| TFFH(15.9 mg) | DB(DMAP)*(28.3 mg) | − | 7 | 0.23 |
| TFFH(15.9 mg) | DB(DMAP)*(28.3 mg) | + | 7 | 0.25 |

*DB(DMAP) = 2,6-di-t-butyl-4-(dimethylamino) pyridine
**TMP = trimethylpyridine (collidine)

EXAMPLE 6

Z—Phe—Val—Pro—NH$_2$

The same method as in Example 5 was utilized except that a first coupling (Fmoc—Val OH) was followed by a second (Z—Phe—OH). For the results see Table 3.

TABLE 3

Assembly of Z-Phe-Val-Pro-NH$_2$ from H-Pro-PAL-PEG-PS, with or without the Universal Ionic Fluoride $(C_6H_5CH_2P(C_6H_5)_3^{\oplus}H_2F_3^{\ominus})$

| CR(amt.) | Base(amt.) | Additive | Preactiv. time(min.) | D-Fhe | D-Val |
|---|---|---|---|---|---|
| HATU(45.6 mg) | DIEA(41.8 μl) | − | 7 | 0.81 | <0.1 |
| TFFH(31.7 mg) | DIEA(41.8 μl) | − | 7 | 0.18 | 0.43 |
| TFFH(31.7 mg) | DIEA(41.8 μl) | + | 7 | 0.19 | <0.1 |

Heretofore, the coupling of histidine was always considered difficult without significant racemization. However, as clearly shown by the following data, the use of the ionic fluoride provides a protective effect.

EXAMPLE 7

Fmoc—His(Trt)—Pro—NH$_2$

The same method was applied except that a single coupling via Fmoc—His(Trt)—OH was examined. The HPLC conditions were the same except for use of an isocratic system made of 24% CH$_3$CN (0.1% TFA)—76%H$_2$O (0.1% TFA). For the results, see Table 4.

TABLE 4

System: Fmoc-His(Trt)-OH + H-Pro-PAL-PEG-PS, with or without the Universal Fluoride Additive $(C_6H_5CH_2P(C_6H_5)_3^{\oplus}H_2F_3^{\ominus})$

| CR(amt.) | Base(amt.) | Additive | Preactiv. time(min) | DL(%) |
|---|---|---|---|---|
| TFFH(31.7 mg) | DIEA(41.8 μL) | − | 7 | 7.40 |
| TFFH(31.7 mg) | DIEA(41.8 μL) | + | 7 | 1.82 |
| TBTU(38.5 mg) | DIEA(41.8 μL) | − | 7 | 2.79 |
| TBTU(38.5 mg) | DIEA(41.8 μL) | + | 7 | 1.45 |
| HATU(45.6 mg) | DIEA(41.8 μL) | − | 7 | 3.24 |
| HATU(45.6 mg) | DIEA(41.8 μL) | + | 7 | 1.52 |

The protective effective provided by the ionic fluoride salt is most clearly shown in the case of the very sensitive histidine case (Table 4). For TFFH the racemization dropped from 7.4 to 1.8% when additive was present. For the base used (DIEA) the values for all three coupling reagents were similar suggesting that the same intermediate is involved. It seems likely that the presence of the complexed protonic species (H$_2$F$_3^{\ominus}$) maintains an appropriate pH for the reaction and avoids the effect seen with the strong base diisopropylethylamine present alone. Similar effects occur for other sensitive amino acids (α-phenylglycine, cysteine, etc.).

The above preferred embodiments and examples are given to illustrate the scope and spirit of the present invention. These embodiments and examples will make apparent to those skilled in the art other embodiments and examples. These other embodiments and examples are within the

What is claimed is:

1. An in situ process for preparing a N--protected amino acid fluoride which comprises mixing a N- protected amino acid or acylating derivative thereof with a fluorinating effective amount of an ionic fluoride salt in the presence of a coupling agent under conditions effective to form said protected amino acid fluoride, wherein the anion of the ionic fluoride salt has the formula:

Ly $(HF)_2F^{\ominus}$, $TG_1G_2G_3F_2$— or $LF^{\ominus}$; wherein z is 1, 2, 3, 4, 5, 6, 7, 8, 9 or 10;
y is 0 or 1;
L is $TG_1G_2G_3G_4$;
T is a group IV element selected from the group consisting of Si, Ge, Sn and Pb; and
$G_1$, $G_2$, $G_3$ and $G_4$ are independently halogen, hydrogen,, alkyl, aryl, arylalkyl, cycloalkyl, or cycloalkylalkyl.

2. The process according to claim 1 wherein the anion of the fluoride salt is $(HF)zF^{\ominus}$ wherein z is 1–10.

3. The process according to claim 1 wherein $G_1$, $G_2$, $G_3$ and $G_4$ are independently alkyl, arylalkyl or aryl.

4. The process according to claim 3 wherein alkyl contains 1–6 carbon atoms.

5. The process accordingly claim 1 wherein z is 1, 2 or 3.

6. The process according to claim 1 wherein the coupling agent is a carbodiimide.

7. The process according to claim 6 wherein the carbodiimide is DCC, DIC, or EDC.

8. The process according to claim 1 wherein the coupling agent has the formula:

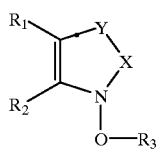 or 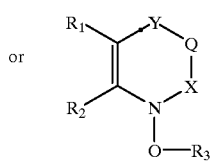

or N-oxides thereof or salt thereof wherein $R_1$ and $R_2$ taken together with the carbon atoms to which they are attached form a heteroaryl ring or aryl ring wherein said heteroaryl ring is an oxygen, sulfur or nitrogen containing heteroaromatic having from 3 and up to a total of 13 ring carbon atoms, said heteroaryl or aryl may be unsubstituted or substituted with lower alkyl or an electron donating group;

Y is O, $NR_4$, $CR_4R_5$;
$R_4$ and $R_5$ are independently hydrogen or lower alkyl;
X is $CR_6R_7$ or $NR_6$;
$R_6$ and $R_7$ are independently hydrogen or lower alkyl or $R_6$ and $R_7$ taken together form an oxo group or when Q is $R_4$ and $R_6$ taken together may form a bond between the nitrogen or carbon atom of Y and the nitrogen or carbon atom of X;
Q is $CR_8R_9$ or $NR_8$;
$R_8$ and $R_9$ are independently hydrogen or lower alkyl or $R_4$ and $R_8$ taken together may form a bond between the ring carbon or nitrogen atom of Q and the ring carbon or nitrogen atom of $R_8$; and
$R_3$ is hydrogen, lower alkyl carbonyl, aryl carbonyl, lower aryl alkyl carbonyl, a positively charged electron withdrawing group, or $SO_2R_{14}$; and $R_{14}$ is hydrogen or lower alkyl.

9. The process according to claim 8 wherein $R_3$ is

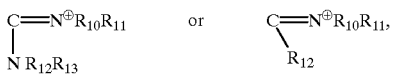

wherein $R_{10}$, $R_{11}$, $R_{12}$ and $R_{13}$ are independently hydrogen, alkyl, or lower alkoxy, lower alkyl or $R_{10}$ and $R_{12}$ taken together with the atoms to which they are attached form a ring so that $R_3$ become

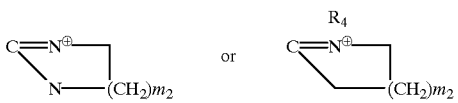

wherein $m_2$ is 0 or 1, or $R_{10}$ and $R_{11}$ taken together with the nitrogen to which they are attached form a 5- or 6-membered heterocyclic ring containing up to 5 carbon ring atoms.

10. The process according to claim 8 wherein the coupling agent is of the formula

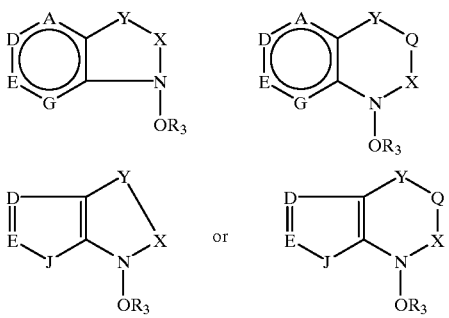

wherein

A is N or $CR_{15}$;
D is $CR_{16}$ or N;
E is $CR_{17}$ or N;
G is $CR_{18}$ or N;
$R_{15}$, $R_{16}$, $R_{17}$ and $R_{18}$ are independently hydrogen, lower alkyl or electron donating group;
J is $NR_{15}$, O, $CR_{15}R_{19}$ or S(O)p;
p is 0, 1 or 2, and
$R_{19}$ is hydrogen or lower alkyl.

11. The process according to claim 10 wherein the coupling agent is of the formula:

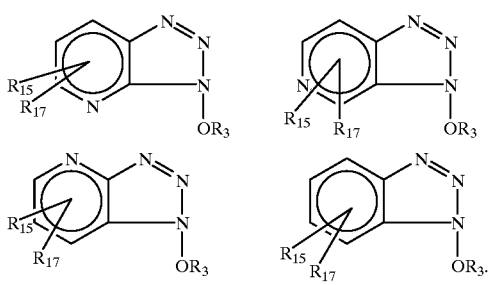

12. The process according to claim 11 wherein $R_3$ is lower alkylcarbonyl,

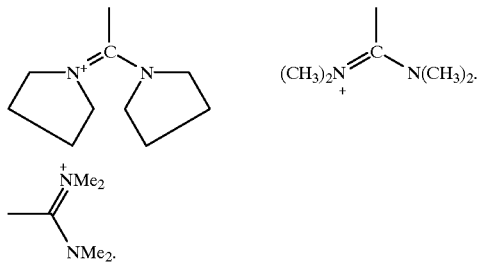

13. The process according to claim 1 wherein the anion of the ionic fluoride is $HF_2^\ominus$, $H_2F_3^\ominus$, $Sn\phi_3F_2^\ominus$, or $H_3F_4^\ominus$, wherein $\phi$ is phenyl.

14. The process according to claim 1 wherein the coupling agent is selected from the group consisting of HBTU, HATU, TBTU, TFFH, DCC, EEDQ and DIC.

15. The process according to claim 1 wherein the anion of the ionic fluoride salt has the formula:
Ly(HF)$_z$ F$^-$ wherein
z is 1, 2, 3, 4, 5, 6, 7, 8, 9, or 10;
y is 0 or 1;
L is $TG_1G_2G_3G_4$;
T is a Group IV element selected from the group consisting of Si, Ge, Sn and Pb; and
$G_1$, $G_2$, $G_3$ and $G_4$ are independently halogen, hydrogen, alkyl, aryl, arylalkyl, cycloalkyl or cycloalkyl alkyl.

16. The process according to claim 15 wherein the anion has the formula $HF_2^-$, $H_2F_3^-$, or $H_3F_4^-$.

17. The process according to claim 15 wherein y is 1.

18. The process according to claim 17 wherein z is 1, 2 or 3.

19. The process according to claim 18 wherein $G_1$, $G_2$, $G_3$ or $G_4$ are independently alkyl, arylalkyl or aryl.

20. The process according to claim 17 wherein T is Sn or Si.

21. The process according to claim 17 wherein $G_1$, $G_2$, $G_3$ and $G_4$ are independently alkyl, arylalkyl or aryl.

22. The process according to claim 1 wherein the cation is an alkali metal, alkaline earth metal, hydrogen, ammonium, $NQ_5Q_6Q_7Q_8^+$, $PQ_5Q_6Q_7Q_8^+$, $SQ_5Q_6Q_7^+$, $HalQ_5Q_6^\oplus$, or

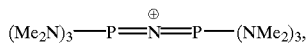

wherein
$Q_5$, $Q_6$, $Q_7$ and $Q_8$ are independently hydrogen, halogen, lower alkyl, aryl or aryl lower alkyl, and Hal is halo.

23. The process according to claim 1 wherein the ionic fluoride salt has the formula:

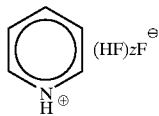

wherein z is 1–6.

24. The process according to claim 1 wherein the ionic salt has the formula $Et_3NH^+(HF)z_4\ F^-$, wherein $z_4$ is 1–3.

25. The process according to claim 22 wherein y is 0.

26. The process according to claim 22 wherein y is 1.

27. The process according to claim 26 wherein T is Sn or Si.

28. The process according to claim 26 wherein $G_1$, $G_2$, $G_3$ and $G_4$ are independently alkyl, arylalkyl or aryl.

29. The process according to claim 22 wherein z is 1–4.

30. The process according to claim 22 wherein the cation is alkali, $N^\oplus Q_5Q_6Q_7Q_8$ or $P^\oplus Q_5Q_6Q_7Q_8$.

31. The process according to claim 1 wherein the ionic fluoride salt is
$(C_6H_5)_4P^\oplus H_2F_3^\ominus$, benzyltriphenylphosphonium dihydrogen trifluoride, $Bu_4N^\oplus HF_2^\ominus$, $Bu_4P^+HF_2^-$, $Bu_4P^+H_2F_3^-$, $(C_6H_5)_4P^\oplus HF_2^-$, $(C_6H_5)_4P^+H_2F_{3-}$, $(C_8H_{17})_4N^+HF_2^-$, or $(C_8H_{17})_4P^+H_2F_3^-$.

32. The process according to claim 31 wherein the ionic salt is benzyltriphenyl phosphonium dihydrogen trifluoride or $(C_6H_5)_4P^\oplus H_2F^\ominus_3$.

33. The process according to claim 1 wherein the anion of the ionic fluoride salt has the formula

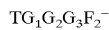

wherein T is a group IV element selected from the group consisting of Si, Ge, Sn and Pb;
$G_1$, $G_2$ and $G_3$ are independently halogen, hydrogen, alkyl, aryl, arylalkyl, cycloalkyl or cycloalkyl.

34. The process according to claim 33 wherein T is Sn or Si.

35. The process according to claim 33 wherein $G_1$, $G_2$ and $G_3$ and are independently alkyl, aryl, or arylalkyl.

36. The process according to claim 34 wherein $G_1$, $G_2$, $G_3$ and $G_4$ are independently alkyl, aryl or arylalkyl.

37. The process according to claim 1 wherein the anion of the ionic fluoride salt has the formula:

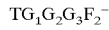

and the cation is an alkali metal, alkali earth metal, hydrogen, ammonium, $NQ_5Q_6Q_7Q_{8+}$, $PQ_5Q_6Q_7Q_8^+$, $SQ_5Q_6Q_6^+$, $HalQ_5Q_6^\oplus$ or

wherein
T is a Group IV element selected from the group consisting of Si, Ge, Sn and Pb;
$G_1$, $G_2$ and $G_3$ are independently halogen, hydrogen, alkyl, aryl, arylalkyl, cycloalkyl or cycloalkyl alkyl; and
$Q_5$, $Q_6$, $Q_7$ and $Q_8$ are independently hydrogen, lower alkyl, aryl or aryl lower alkyl and Hal is halo.

38. The process according to claim 37 wherein T is Sn or Si.

39. The process according to claim 37 wherein $G_1$, $G_2$, $G_3$, and $G_4$ are independently alkyl or aryl alkyl or aryl.

40. The process according to claim 37 wherein the ionic fluoride salt has the formula:

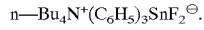

41. A process for forming a peptide between a N- -amino protected amino acid or acylating derivative thereof and a second amino acid with a free amino group or a peptide containing a free amino group, which process comprises:
(a) mixing in situ said N- -amino protected amino acid with a fluorinating effective amount of an ionic fluoride salt in the presence of a coupling agent under conditions effective to form a N--amino protected amino acid fluoride, and (b) reacting the product of (a) with said second amino acid or peptide under peptide forming conditions, wherein the anion of the ionic fluoride salt has the formula:

$$Ly_y(HF)_zF^-, TG_1G_2G_3F_2^- \text{ or } LF^\ominus;$$

wherein z is 1, 2, 3, 4, 5, 6, 7, 8, 9 or 10;

y is 0 or 1;

L is $TG_1G_2G_3G_4$;

T is a group IV element selected from the group consisting of Si, Ge, Sn and Pb; and $G_1$, $G_2$, $G_3$ $G_4$ are independently halogen, hydrogen, alkyl, aryl, arylalkyl, cycloalkyl, or cycloalkylalkyl.

42. The process according to claim 41 wherein $G_1$, $G_2$, $G_3$ and $G_4$ are independently alkyl, arylalkyl or aryl.

43. The process according to claim 42 wherein alkyl contains 1–6 carbon atoms.

44. The process according to claim 41 wherein z is 1, 2, or 3.

45. The process according to claim 41 wherein the coupling agent is a carbodiimide.

46. The process according to claim 45 wherein the carbodiimide is DCC, DIC, or EDC.

47. The process according to claim 41 wherein the coupling agent has the formula:

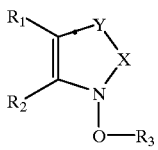 or 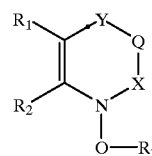

or N-oxides thereof or salt thereof wherein $R_1$ and $R_2$ taken together with the carbon atoms to which they are attached form a heteroaryl ring or aryl ring wherein said heteroaryl ring is an oxygen, sulfur or nitrogen containing heteroaromatic having from 3 and up to a total of 13 ring carbon atoms, said heteroaryl or aryl may be unsubstituted or substituted with lower alkyl or an electron donating group;

Y is O, $NR_4$, $CR_4R_5$;

$R_4$ and $R_5$ are independently hydrogen or lower alkyl;

X is $CR_6R_7$ or $NR_6$;

$R_6$ and $R_7$ are independently hydrogen or lower alkyl or $R_6$ and $R_7$ taken together form an oxo group or hen Q is not present, $R_4$ and $R_6$ taken together may form a bond between the nitrogen or carbon atom of Y and the nitrogen or carbon atom of X;

Q is $CR_8R_9$ or $NR_8$;

$R_8$ and $R_9$ are independently hydrogen or lower alkyl or $R_4$ and $R_8$ taken together may form a bond between the ring carbon or nitrogen atom of Q and the ring carbon or nitrogen atom of $R_8$; and $R_3$ is lower alkyl carbonyl, aryl carbonyl, lower aryl alkyl carbonyl, a positively charged electron withdrawing group, or $SO_2R_{14}$ and $R_{14}$ is hydrogen or lower alkyl.

48. The process according to claim 47 wherein $R_3$ is

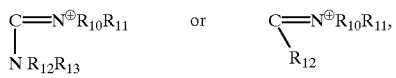

wherein $R_{10}$, $R_{11}$, $R_{12}$ and $R_{13}$ are independently hydrogen, alkyl, or lower alkoxy lower alkyl or $R_{10}$ and $R_{12}$ taken together with the atoms to which they are attached form a ring so that $R_3$ become

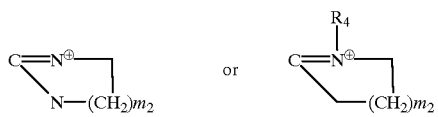

wherein $m_2$ is 0 or 1 or $R_{10}$ and $R_{11}$ taken together with the nitrogen atom to which they are attached form a 5- or 6-membered heterocyclic ring containing up to 5 ring carbon atoms.

49. The process according to claim 47 wherein the coupling agent is of the formula

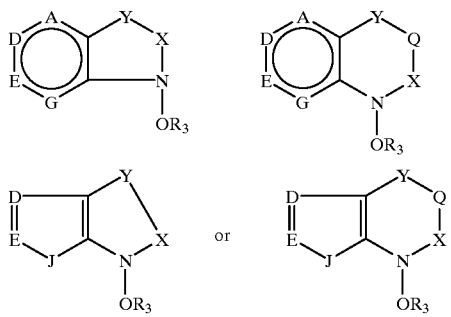

wherein

A is N or $CR_{15}$;

D is $CR_{16}$ or N;

E is $CR_{17}$ or N;

G is $CR_{18}$ or N;

$R_{15}$, $R_{16}$, $R_{17}$ and $R_{18}$ are independently hydrogen lower alkyl or electron donating group;

J is $NR_{15}$, O, $CR_{15}R_{19}$ or $S(O)p$;

p is 0, 1 or 2, and $R_{19}$ is hydrogen or lower alkyl.

50. The process according to claim 49 wherein the coupling agent is of the formula:

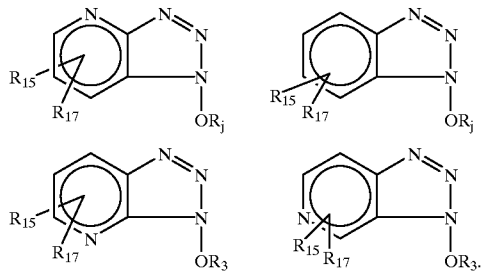

51. The process according to claim 49 wherein $R_3$ is lower alkyl,

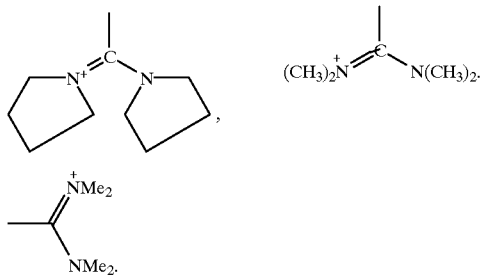

52. The process according to claim 41 wherein the anion of the ionic fluoride is $HF_2^{\ominus}$, $H_2F_3^{\ominus}$, $Sn\phi_3F_2^{\ominus}$ or $H_3F_2^-$, wherein $\phi$ is phenyl.

53. The process according to claim 41 wherein the coupling agent is selected from the group consisting of HBTU, HATU, TBTU, TFFH, DCC, EEDQ, EDC and DIC.

54. In the improved process for forming an organic acid fluoride in situ, from an organic acid, the improvement comprising reacting said organic acid with a fluorinating effective amount of an ionic fluoride salt in the presence of a peptide coupling agent, under conditions effective to form said organic acid fluoride, wherein the anion of the ionic fluoride salt has the formula:

$Ly(HF)_zF^-$, $TG_1G_2G_3F_2^-$ or $LF^{\ominus}$, wherein z is 1, 2, 3, 4, 5, 6, 7, 8, 9 or 10;

y is 0 or 1;

L is $TG_1G_2G_3G_4$;

T is a group IV element selected from the group consisting of Si, Ge, Sn and Pb; and $G_1$, $G_2$, $G_3$ $G_4$ are independently halogen, hydrogen, alkyl, aryl, arylalkyl, cycloalkyl, or cycloalkylalkyl.

55. The improved process according to claim 54 wherein the organic acid is a hydrocarbyl organic acid.

56. In the synthesis of a peptide wherein a first N--amino protected amino acid is covalently coupled to a solid phase peptide synthesis resin, the N--amino protecting group is cleaved off and the resulting free amino group is reacted under amide forming conditions with a N--amino protected amino acid fluoride, the resulting N--amino protecting group is cleaved off and coupled to another protected amino acid fluoride and the cycle repeated until the desired peptide has been obtained, and then the peptide is cleaved from said resin, the improvement comprising preparing said amino acid fluoride in situ by reacting a N--amino protected amino acid or acylating derivative thereof with a fluorinating effective amount of an ionic fluoride salt in the presence of a coupling agent, under conditions effective to form said protected amino acid fluoride, wherein the anion of the ionic fluoride salt has the formula: $Ly(HF)_2Fe^{\ominus}$, $LF^{\ominus}$ or $TG_1G_2G_3F_2^-$;

wherein z is 1, 2, 3, 4, 5, 6, 7, 8, 9 or 10;

y is 0 or 1;

L is $TG_1G_2G_3G_4$;

$G_1$, $G_2$, $G_3$ and $G_4$ are independently halogen, hydrogen, alkyl, aryl, aryl alkyl, cycloalkyl or cycloalkylalkyl; and T is a Group IV element selected from the group consisting of Si, Ge, Sn, and Pb.

57. The improved process according to claim 56, wherein the anion of the ionic fluoride salt is $(HF)_zF^{\ominus}$, wherein z is 1–10.

58. In a process for forming an amide from the reaction of an organic amine and a carboxylic acid fluoride, the improvement comprising forming the carboxylic acid fluoride in situ by reacting a carboxylic acid or acylating derivative thereof with a fluorinating effective amount of an ionic fluoride salt in the presence of a peptide coupling agent under conditions effective to form said carboxylic acid fluoride, which is then reacted with the organic amine to form said amide, wherein the anion of the fluoride salt has the formula:

$Ly(HF)_zF^{\ominus}$, $TG_1G_2G_3G_4F_2^-$ or $LF^-$;

wherein z is 1–10;

y is 0 or 1;

L is $TG_1G_2G_3G_4$;

T is a Group IV element selected from the group consisting of Si, Ge, Sn and Pb; and $G_1$, $G_2$, $G_3$ and $G_4$ are independently halogen, hydrogen alkyl, aryl, arylalkyl, cycloalkyl or cycloalkylalkyl.

59. The process according to claim 58 wherein the anion of the ionic fluoride salt is $(HF)_zF^{\oplus}$, wherein z is 1, 2, 3, 4, 5, 6, 7, 8, 9 or 10.

60. A solution comprising a fluorinating effective amount of an ionic fluoride salt having an ionizable fluoride, a coupling agent and an N--amino protected amino acid or acylating derivative thereof, wherein the anion of the ionic fluoride salt has the formula:

$Ly(HF)_zF^-$, $TG_1G_2G_3F_2^-$ or $LF^{\ominus}$;

wherein z is 1, 2, 3, 4, 5, 6, 7, 8, 9 or 10;

y is 0 or 1;

L is $TG_1G_2G_3G_4$; and

T is a Group IV element selected from the group consisting of Si, Ge, Sn and Pb; and $G_1$, $G_2$, $G_3$ and $G_4$ are independently hydrogen, alkyl, aryl, arylalkyl, cycloalkyl or cycloalkylalkyl, wherein the fluoride salt, coupling agent and Nocamino protected amino acid or acylating derivative are capable of forming a N--amino acid fluoride in situ.

61. The solution according to claim 60 wherein the anion of the ionic fluoride salt is $(HF)_zF^{\ominus}$, wherein z is 1–10.

62. The solution according to claim 60 wherein z is 1, 2, 3 or 4.

63. The solution according to claim 60 wherein the coupling agent is a carbodimide.

64. The solution according to claim 63 wherein the carbodimide is DCC, DIC or EDC.

65. The solution according to claim 60 wherein the coupling agent has the formula

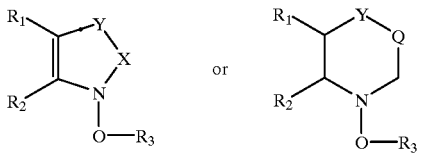

or N-oxides thereof or salt thereof wherein

R₁ and R₂ taken together with the carbon atoms to which they are attached form a heteroaryl ring or aryl ring wherein said heteroaryl ring is an oxygen, sulfur or nitrogen containing heteroaromatic having from 3 and up to a total of 13 ring carbon atoms, said heteroaryl or aryl may be unsubstituted or substituted with lower alkyl or an electron donating group;

Y is O, NR₄, CR₄R₅;

R₄ and R₅ are independently hydrogen or lower alkyl;

X is CR₆R₇ or NR₆;

R₆ and R₇ are independently hydrogen or lower alkyl or R₆ and R₇ taken together form an oxo group or when Q is not present, R₄ and R₆ taken together may form a bond between the nitrogen or carbon atom of Y and the nitrogen or carbon atom of X;

Q is CR₈R₉ or NR₈;

R₈ and R₉ are independently hydrogen or lower alkyl or R₄ and R₈ taken together may form a bond between the ring carbon or nitrogen atom of Q and the ring carbon or nitrogen atom of R₈; and R₃ is lower alkyl carbonyl, aryl carbonyl, lower aryl alkyl carbonyl, a positively charged electron withdrawing group, or SO₂R₁₄; and R₁₄ is hydrogen or lower alkyl.

66. The solution according to claim 60 wherein the anion of the ionic fluoride is $HF_2^-$, $H_2F_3^-$, $H_3F_4^-$ or $Sn\phi_3F_2^-$, wherein φ is phenyl.

67. The solution according to claim 60 wherein the ionic fluoride salt is benzyl triphenylphosphonoim dihydrogen trifluoride.

68. The solution according to claim 60 wherein a α-carboxy protected amino acid having a free α-amino group is additionally present.

69. The solution according to claim 60 wherein a peptide having a free-α-amino group is additionally present.

70. The solution according to claim 60 wherein the anion of the fluoride salt has the formula:

Ly(HF)$_z$ F⁻ wherein z is 1, 2, 3, 4, 5, 6, 7, 8, 9, or 10;

y is 0 or 1;

L is TG₁G₂G₃G₄;

T is a Group IV element selected from the group consisting of Si, Ge, Sn and Pb; and G₁, G₂, G₃ and G₄ are independently halogen, hydrogen, alkyl, aryl, enyl alkyl, cycloalkyl or cycloalkyl.

71. The solution according to claim 70 wherein y is 0.

72. The solution according to claim 70 wherein y is 1.

73. The solution according to claim 72 wherein G₁, G₂, G₃ and G₄ are independently, alkyl, arylalkyl or aryl.

74. The solution according to claim 72 wherein T is Sn or Si.

75. The solution according to claim 70 wherein the anion of the ionic fluoride salt has the formula:

TG₁G₂G₃F₂⁻.

76. The solution according to claim 75 wherein T is Sn or Si.

77. The solution according to claim 75 wherein G₁, G₂ and G₃ are independently alkyl, aryl or arylalkyl.

78. The solution according to claim 60 wherein the ionic fluoride salt has the formula

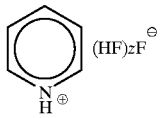

wherein z is 1–6.

79. The solution according to claim 60 wherein the ionic fluoride salt has the formula Et₃NH⁺(HF)z₄F⁻, wherein z₄ is 1–3.

80. The solution according to claim 60 wherein the ionic fluoride salt is $(C_6H_5)_4P^\oplus H_2F_3^\ominus$, benzyltriphenylphosphonium dihydrogen trifluoride, $Bu_4N^\oplus HF_2^\ominus$, $Bu_4P^+HF_2^-$, $Bu_4P^+H_2F_3^-$, $(C_6H_5)_4P^\oplus HF_2^-$, $(C_6H_5)_4P^+H_2F_3^-$, $(C_8H_{17})_4N^+HF_2^-$, or $(C_8H_{17})_4P^+H_2F_3^-$.

81. The solution according to claim 60 wherein the ionic fluoride salt is $(C_6H_5)_3 (C_6H_5CH_2)P^\oplus H_2F^-_3$, $(C_6H_5)_4P^\oplus H_2F^-_3$ or n—$Bu_4N^+(C_6H_5)_3SnF_2^-$.

82. A kit useful for preparing amino acid fluorides in situ comprising an ionic fluoride salt and an N--amino protected amino acid, the contents of said kit, when mixed with a coupling agent in solution, generates an amino acid fluoride in situ, the anion of the ionic fluoride salt having the formula:

Ly(HF)₂F⁻, TG₁G₂G₃F₂⁻ or LF⁻;

wherein z is 1, 2, 3, 4, 5, 6, 7, 8, 9 or 10;

y is 0 or 1;

L is TG₁G₂G₃G₄;

T is a Group IV element selected from the group consisting of Si, Ge, Sn and Pb; and G₁, G₂, G₃ and G₄ are independently halogen, hydrogen, alkyl, aryl, arylalkyl, cycloalkyl or cycloalkylalkyl.

83. A kit useful for preparing amino acid fluorides in situ comprising an ionic fluoride salt in one compartment and a coupling agent in a different compartment, the contents of said kit when mixed with an N--amino-protected amino acid or acylating derivative in solution generates an N--amino protected-amino acid fluoride in situ, the anion of the ionic fluoride salt having the formula:

Ly(HF)₂F⁻, TG₁G₂G₃F₂⁻ or LF⁻;

wherein z is 1, 2, 3, 4, 5, 6, 7, 8, 9 or 10;

v is 0 or 1 ;

L is TG₁G₂G₃G₄;

T is a Group IV element selected from the group consisting of Si, Ge, Sn and Pb; and $G_1$, $G_2$, $G_3$ and $G_4$ are independently halogen, hydrogen, alkyl, aryl, arylalkyl, cycloalkyl or cycloalkylalkyl.

84. The kit according to claim 82 wherein the ionic fluoride salt is admixed with the N-α-amino protected amino acid.

85. The kit according to claim 82 wherein the ionic fluoride salt is in one compartment and the N-α-amino protected amino acid is in a second compartment.

86. The kit according to claim 84 wherein the coupling agent is additionally present in a second compartment.

87. The kit according to claim 85 wherein the coupling agent is additionally present in a third compartment.

88. The kit according to claim 82, wherein the anion of the ionic fluoride salt is $(HF)_zF^\ominus$, wherein z is 1–10.

89. A process for forming an amino acid fluoride in situ comprising reacting a fluorinating effective amount of an ionic fluoride salt with a mixed anhydride of a N- -amino acid, under conditions effective to form said amino acid fluoride, wherein the anion of the ionic fluoride salt has the formula:

$$Ly(HF)_zF^-, TG_1G_2G_3F_2^- \text{ or } LF^\ominus;$$

wherein
z is 1, 2, 3, 4, 5, 6, 7, 8, 9 or 10;
y is 0 or 1;
L is $TG_1G_2G_3G_4$;
T is a Group IV element selected from the group consisting of Si, Ge, Sn and Pb; and
$G_1$, $G_2$, $G_3$ and $G_4$ are independently halogen, hydrogen, alkyl, aryl, arylalkyl, cycloalkyl or cycloalkylalkyl.

90. The process according to claim 89 wherein the mixed anhydride is a lower carbonic acid ester of a N-α-amino protected amino acid and an acid under esterifying conditions, wherein the acid is carbonic acid, lower alkyl mono ester of carbonic acid, carbonic acid monoamide, N-lower alkyl carbonic acid amide, N, N-diloweralkyl carbonic acid monoamide or trimethylacetic acid.

91. The process according to claim 89 wherein the anion of the ionic fluoride salt is $(HF)_zF^\ominus$, wherein z is 1–10.

92. The process according to claim 89 wherein the anion of the ionic fluoride salt is $HF_2^-$, $H_2F_3^-$, $H_3F_4^-$, or $Sn\phi_3F_2^-$, wherein ϕ is phenyl.

93. A process for forming an amino acid fluoride in situ comprising reacting under fluorination conditions a fluorinating effective amount of an ionic fluoride salt with an active ester of an N- -amino protected amino acid, under conditions effective to form said amino acid fluoride, wherein the anion of the ionic fluoride salt has the formula:

$$Ly(HF)_zF^-, TG_1G_2G_3F_2^- \text{ or } LF^\ominus;$$

wherein
z is 1, 2, 3, 4, 5, 6, 7, 8, 9 or 10;
y is 0 or 1,
L is $TG_1G_2G_3G_4$;
T is a Group IV element selected from the group consisting of Si, Ge, Sn and Pb; and
$G_1$, $G_2$, $G_3$ and $G_4$ are independently halogen, hydrogen, alkyl, aryl, arylalkyl, cycloalkyl or cycloalkylalkyl.

94. The process according to claim 93 wherein the active ester is an N-α-hydroxy succinimide of N-α-amino protected amino acid, N-hydroxy piperidine ester of N-α-amino protected amino acid or N-α-hydroxy-phthalimide ester of N-α-amino protected amino acid.

95. The process according to claim 93 wherein the active ester has the formula:
$(W)m_1Ar\ O—AA_1—BLK_1$

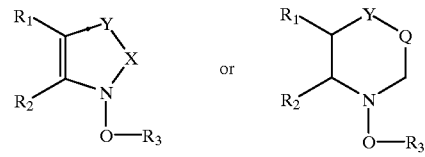

wherein
$R_1$ and $R_2$ taken together with the carbon atoms to which they are attached form a heteroaryl ring or aryl ring wherein said heteroaryl ring is an oxygen, sulfur or nitrogen containing heteroaromatic having from 3 and up to a total of 13 ring carbon atoms, said heteroaryl or aryl may be unsubstituted or substituted with lower alkyl or an electron donating group;
Y is O, $NR_4$, $CR_4R_5$;
$R_4$ and $R_5$ are independently hydrogen or lower alkyl;
X is $CR_6R_7$ or $NR_6$;
$R_6$ and $R_7$ are independently hydrogen or lower alkyl or $R_6$ and $R_7$ taken together form an oxo group or when Q is not present $R_4$ and $R_6$ taken together may form a bond between the nitrogen or carbon atom of Y and the nitrogen or carbon atom of X;
Q is $CR_8R_9$ or $NR_8$;
$R_8$ and $R_9$ are independently hydrogen or lower alkyl or $R_4$ and $R_8$ taken together may form a bond between the ring carbon or nitrogen atom of Q and the ring carbon or nitrogen atom of $R_8$; and
Ar is aryl,
$R_3$ is $BLK_1—AA_1$,
$BLK_1$ is an N-α-amino protecting group,
$AA_1$ is an amino acid residue,
W is an electron withdrawing group; and
$m_1$ is an integer from 1–5.

96. The process according to claim 95 wherein aryl is phenyl.

97. The process according to claim 93 wherein the anion of the ionic fluoride salt is $(HF)_zF^\ominus$, wherein z is 1–10.

98. The process according to claim 93 wherein the anion of the ionic fluoride salt is $HF_2^\oplus$, $H_2F_3^-$, $H_3F_4^-$ or $Sn\phi_3F_2^-$, wherein ϕ is phenyl.

* * * * *